(12) United States Patent
Ferree et al.

(10) Patent No.: US 9,731,126 B2
(45) Date of Patent: Aug. 15, 2017

(54) TRANSCUTANEOUS ELECTRICAL NERVE STIMULATOR WITH AUTOMATIC DETECTION OF LEG ORIENTATION AND LEG MOTION FOR ENHANCED SLEEP ANALYSIS, INCLUDING ENHANCED TRANSCUTANEOUS ELECTRICAL NERVE STIMULATION (TENS) USING THE SAME

(71) Applicant: Neurometrix, Inc., Waltham, MA (US)

(72) Inventors: Thomas Ferree, Waltham, MA (US); Shai Gozani, Brookline, MA (US); Xuan Kong, Acton, MA (US)

(73) Assignee: Neurometrix, Inc., Waltham, MA (US)

( * ) Notice: Subject to any disclaimer, the term of this patent is extended or adjusted under 35 U.S.C. 154(b) by 0 days.

(21) Appl. No.: 14/980,041

(22) Filed: Dec. 28, 2015

(65) Prior Publication Data

US 2016/0144174 A1 May 26, 2016

Related U.S. Application Data

(63) Continuation-in-part of application No. 14/794,588, filed on Jul. 8, 2015, now Pat. No. 9,675,801, which
(Continued)

(51) Int. Cl.
*A61N 1/36* (2006.01)
*A61N 1/04* (2006.01)
(Continued)

(52) U.S. Cl.
CPC ........ *A61N 1/36021* (2013.01); *A61B 5/1116* (2013.01); *A61B 5/4815* (2013.01);
(Continued)

(58) Field of Classification Search
CPC .............. A61N 1/36021; A61N 1/0456; A61B 5/1116; A61B 5/4815; A61B 5/6828; A61B 5/6831
See application file for complete search history.

(56) References Cited

U.S. PATENT DOCUMENTS

| 4,503,863 A | 3/1985 | Katims |
| 4,605,010 A | 8/1986 | McEwen |

(Continued)

FOREIGN PATENT DOCUMENTS

| CN | 101626804 | 1/2010 |
| CN | 102355847 | 2/2012 |

(Continued)

OTHER PUBLICATIONS

Ancoli-Israeli S. et al., The Role of Actigraphy in the Study of Sleep and Circadian Rhythms, Sleep, 2003, 26(3), p. 342-392.
(Continued)

*Primary Examiner* — Catherine Voorhees
(74) *Attorney, Agent, or Firm* — Pandiscio & Pandiscio

(57) ABSTRACT

Apparatus for providing transcutaneous electrical nerve stimulation (TENS) therapy to a user, the apparatus comprising: a housing; an application unit for providing mechanical coupling between the housing and the user's body; a stimulation unit for electrically stimulating at least one nerve of the user; a sensing unit for sensing the user's body movement and body orientation; and a reporting unit for providing the user with feedback based on the user's sensed body movement and body orientation.

57 Claims, 10 Drawing Sheets

Related U.S. Application Data is a continuation-in-part of application No. 14/610,757, filed on Jan. 30, 2015, now Pat. No. 9,656,070, which is a continuation of application No. 13/678,221, filed on Nov. 15, 2012, now Pat. No. 8,948,876, said application No. 14/794,588 is a continuation-in-part of application No. 14/269,887, filed on May 5, 2014, which is a continuation-in-part of application No. 14/230,648, filed on Mar. 31, 2014, now Pat. No. 9,474,898, said application No. 14/269,887 is a continuation-in-part of application No. 14/253,628, filed on Apr. 15, 2014.

(60) Provisional application No. 61/560,029, filed on Nov. 15, 2011, provisional application No. 61/657,382, filed on Jun. 8, 2012, provisional application No. 61/806,481, filed on Mar. 29, 2013, provisional application No. 61/811,864, filed on Apr. 15, 2013, provisional application No. 61/819,159, filed on May 3, 2013, provisional application No. 61/858,150, filed on Jul. 25, 2013, provisional application No. 62/021,807, filed on Jul. 8, 2014, provisional application No. 62/213,978, filed on Sep. 3, 2015, provisional application No. 62/101,029, filed on Jan. 8, 2015.

(51) Int. Cl.
*A61B 5/11* (2006.01)
*A61B 5/00* (2006.01)
*A61N 1/32* (2006.01)

(52) U.S. Cl.
CPC .......... *A61B 5/6828* (2013.01); *A61B 5/6831* (2013.01); *A61N 1/0456* (2013.01); *A61N 1/0476* (2013.01); *A61N 1/0492* (2013.01); *A61N 1/321* (2013.01); *A61N 1/36014* (2013.01)

(56) References Cited

U.S. PATENT DOCUMENTS

| | | | |
|---|---|---|---|
| 4,738,250 | A | 4/1988 | Fulkerson et al. |
| 5,063,929 | A | 11/1991 | Bartelt et al. |
| 5,169,384 | A | 12/1992 | Bosniak et al. |
| 5,350,414 | A | 9/1994 | Kolen |
| 5,487,759 | A | 1/1996 | Bastyr et al. |
| 5,562,718 | A | 10/1996 | Palermo |
| 5,806,522 | A | 9/1998 | Katims |
| 5,948,000 | A | 9/1999 | Larsen et al. |
| 6,161,044 | A | 12/2000 | Silverstone |
| 6,266,558 | B1 | 7/2001 | Gozani et al. |
| 6,430,450 | B1 | 8/2002 | Bach-y-Rita et al. |
| 6,456,884 | B1 | 9/2002 | Kenney |
| 6,662,051 | B1 | 12/2003 | Eraker et al. |
| 7,668,598 | B2 | 2/2010 | Herregraven et al. |
| 7,720,548 | B2 | 5/2010 | King |
| 7,725,193 | B1 | 5/2010 | Chu |
| 8,108,049 | B2 | 1/2012 | King |
| 8,121,702 | B2 | 2/2012 | King |
| 8,131,374 | B2 | 3/2012 | Moore et al. |
| 8,421,642 | B1* | 4/2013 | McIntosh ............... G06F 3/017 340/539.1 |
| 8,825,175 | B2 | 9/2014 | King |
| 8,862,238 | B2 | 10/2014 | Rahimi et al. |
| 8,948,876 | B2 | 2/2015 | Gozani et al. |
| 9,168,375 | B2 | 10/2015 | Rahimi et al. |
| 2002/0010497 | A1 | 1/2002 | Merfeld et al. |
| 2003/0023192 | A1 | 1/2003 | Foxlin |
| 2003/0074037 | A1 | 4/2003 | Moore et al. |
| 2003/0114892 | A1 | 6/2003 | Nathan et al. |
| 2003/0208246 | A1 | 11/2003 | Kotlik et al. |
| 2005/0059903 | A1 | 3/2005 | Izumi |
| 2005/0080463 | A1 | 4/2005 | Stahmann et al. |
| 2006/0052788 | A1 | 3/2006 | Thelen et al. |
| 2006/0085049 | A1 | 4/2006 | Cory et al. |
| 2006/0095088 | A1 | 5/2006 | De Ridder |
| 2006/0173507 | A1 | 8/2006 | Mrva et al. |
| 2006/0190057 | A1 | 8/2006 | Reese |
| 2007/0060922 | A1 | 3/2007 | Dreyfuss |
| 2007/0276449 | A1 | 11/2007 | Gunter et al. |
| 2008/0077192 | A1 | 3/2008 | Harry et al. |
| 2008/0146980 | A1 | 6/2008 | Rousso et al. |
| 2008/0147146 | A1 | 6/2008 | Wahlgren et al. |
| 2009/0030476 | A1 | 1/2009 | Hargrove |
| 2009/0112214 | A1 | 4/2009 | Philippon et al. |
| 2009/0131993 | A1 | 5/2009 | Rousso et al. |
| 2009/0240303 | A1 | 9/2009 | Wahlstrand et al. |
| 2009/0264789 | A1 | 10/2009 | Molnar et al. |
| 2009/0270947 | A1 | 10/2009 | Stone et al. |
| 2009/0326604 | A1 | 12/2009 | Tyler et al. |
| 2010/0042180 | A1 | 2/2010 | Mueller et al. |
| 2010/0057149 | A1 | 3/2010 | Fahey |
| 2010/0087903 | A1 | 4/2010 | Van Herk et al. |
| 2010/0094103 | A1 | 4/2010 | Kaplan et al. |
| 2010/0114257 | A1 | 5/2010 | Torgerson |
| 2010/0198124 | A1 | 8/2010 | Bhugra |
| 2010/0241464 | A1* | 9/2010 | Amigo ............... G06Q 40/08 705/4 |
| 2011/0066209 | A1 | 3/2011 | Bodlaender et al. |
| 2011/0224665 | A1 | 9/2011 | Crosby et al. |
| 2011/0257468 | A1 | 10/2011 | Oser et al. |
| 2011/0264171 | A1 | 10/2011 | Torgerson |
| 2011/0276107 | A1 | 11/2011 | Simon et al. |
| 2011/0282164 | A1 | 11/2011 | Yang et al. |
| 2012/0010680 | A1 | 1/2012 | Wei et al. |
| 2012/0108998 | A1 | 5/2012 | Molnar et al. |
| 2013/0096641 | A1 | 4/2013 | Strother et al. |
| 2013/0158627 | A1 | 6/2013 | Gozani et al. |
| 2014/0163444 | A1* | 6/2014 | Ingvarsson ........... A61F 5/0102 602/2 |
| 2014/0296934 | A1 | 10/2014 | Gozani et al. |
| 2014/0296935 | A1 | 10/2014 | Ferree et al. |
| 2014/0309709 | A1* | 10/2014 | Gozani ............... A61N 1/36021 607/46 |
| 2014/0336730 | A1* | 11/2014 | Simon ................ A61N 1/36014 607/72 |
| 2015/0321000 | A1 | 11/2015 | Rosenbluth et al. |
| 2015/0335288 | A1* | 11/2015 | Toth ..................... A61B 5/6833 600/373 |

FOREIGN PATENT DOCUMENTS

| | | |
|---|---|---|
| CN | 102740919 | 10/2012 |
| DE | 102010052710 | 5/2012 |
| WO | WO 99/64105 | 12/1999 |
| WO | WO 03/051453 | 6/2003 |
| WO | WO 2008/079757 | 7/2008 |
| WO | WO 2008/088985 | 7/2008 |
| WO | WO 2011/075179 | 6/2011 |
| WO | WO 2012/116407 | 9/2012 |

OTHER PUBLICATIONS

Barbarisi, Manlio et al., Pregabalin and Transcutaneous Electrical Nerve Stimulation for Postherpetic Neuralgia Treatment, The Clinical Journal of Pain, Sep. 2010;26(7):567-572.

Bjordal JM et al., Transcutaneous electrical nerve stimulation (TENS) can reduce postoperative analgesic consumption. A meta-analysis with assessment of optimal treatment parameters for postoperative pain, European Journal of Pain, 2003, vol. 7(2): 181-188.

Bloodworth DM et al., Comparison of stochastic vs. conventional transcutaneous electrical stimulation for pain modulation in patients with electromyographically documented radiculopathy, American Journal of Physical Medicine & Rehabilitation, 2004, vol. 83(8): 584-591.

Chandran P et al., Development of opioid tolerance with repeated transcutaneous electrical nerve stimulation administration, Pain, 2003, vol. 102: 195-201.

(56) References Cited

OTHER PUBLICATIONS

Chen CC et al., A comparison of transcutaneous electrical nerve stimulation (TENS) at 3 and 80 pulses per second on cold-pressor pain in healthy human participants, Clinical Physiology and Functioning Imaging, 2010, vol. 30(4): 260-268.
Chen CC et al., An investigation into the effects of frequency-modulated transcutaneous electrical nerve stimulation (TENS) on experimentally-induced pressure pain in healthy human participants, The Journal of Pain, 2009, vol. 10(10): 1029-1037.
Chen CC et al., Differential frequency effects of strong nonpainful transcutaneous electrical nerve stimulation on experimentally induced ischemic pain in healthy human participants, The Clinical Journal of Pain, 2011, vol. 27(5): 434-441.
Chen CC et al., Does the pulse frequency of transcutaneous electrical nerve stimulation (TENS) influence hypoalgesia? A systematic review of studies using experimental pain and healthy human participants, Physiotherapy, 2008, vol. 94: 11-20.
Claydon LS et al., Dose-specific effects of transcutaneous electrical nerve stimulation on experimental pain, Clinical Journal of Pain, 2011, vol. 27(7): 635-647.
Cole, R.J. et al., Automatic Sleep/Wake Identification From Wrist Activity, Sleep, 1992, 15(5), p. 461-469.
Cruccu G. et al., EFNS guidelines on neurostimuiation therapy for neuropathic pain, European Journal of Neurology, 2007, vol. 14: 952-970.
Davies HTO et al., Diminishing returns or appropriate treatment strategy?—an analysis of short-term outcomes after pain clinic treatment, Pain, 1997, vol. 70: 203-208.
Desantana JM et al., Effectiveness of transcutaneous electrical nerve stimulation for treatment of hyperalgesia and pain, Curr Rheumatol Rep. 2008, vol. 10(6): 492-499.
Dubinisky RM et al., Assessment: Efficacy of transcutaneous electric nerve stimulation in the treatment of pain in neurologic disorders (an evidence-based review): Report of the therapeutics and technology assessment subcommittee of the american academy of neurology, Neurology, 2010, vol. 74. 173-176.
Fary RE et al., Monophasic electrical stimulation produces high rates of adverse skin reactions in healthy subjects, Physiotherapy Theory and Practice, 2011, vol. 27(3): 246-251.
Fishbain, David A. et al. Does Pain Mediate the Pain interference with Sleep Problem in Chronic Pain? Findings from Studies for Management of Diabetic Peripheral Neuropathic Pain with Duloxetine, Journal of Pain Symptom Management, Dec. 2008;36(6):639-647.
Fishbain, David A. et al., Transcutaneous Electrical Nerve Stimulation (TENS) Treatment Outcome in Long-Term Users, The Clinical Journal of Pain, Sep. 1996;12(3):201-214.
Food and Drug Administration, Draft Guidance for Industry and Staff: Class II Special Controls Guidance Document: Transcutaneous Electrical Nerve Stimulator for Pain Relief, Apr. 5, 2010.
Garrison DW et al., Decreased activity of spontaneous and noxiously evoked dorsal horn cells during transcutaneous electrical nerve stimulation (TENS), Pain, 1994, vol. 58: 309-315.
Gilron, I. et al., Chronobiological Characteristics of Neuropathic Pain: Clinical Predictors of Diurnal Pain Rhythmicity, The Clinical Journal of Pain, 2013.
Hori, T. et al., Skin Potential Activities and Their Regional Differences During Normal Sleep in Humans, The Japanese Journal of Physiology, 1970, vol. 20, p. 657-671.
Jelinek HF et al., Electric pulse frequency and magnitude of perceived sensation during electrocutaneous forearm stimulation, Arch Phys Med Rehabil, 2010, vol. 91: 1372-1382.
Jin DM et al., Effect of transcutaneous electrical nerve stimulation on symptomatic diabetic peripheral neuropathy: a meta-analysis of randomized controlled trials, Diabetes Research and Clinical Practice, 2010, vol. 89: 10-15.
Johnson MI et al., Analgesic effects of different frequencies of transcutaneous electrical nerve stimulation on cold-induced pain in normal subjects, Pain, 1989, vol. 39: 231-236.

Johnson MI et al., Transcutaneous Electrical Nerve Stimulation (TENS) and TENS-like devices: do they provide pain relief?, Pain Reviews, 2001, vol. 8: 7-44.
Johnson MI et al., Transcutaneous electrical nerve stimulation for the management of painful conditions: focus on neuropathic pain, Expert Review of Neurotherapeutics, 2011, vol. 11(5): 735-753.
Johnson, M.I. et al., An in-depth study of long-term users of transcutaneous electrical nerve stimulation (TENS). Implications for clinical use of TENS. Pain. Mar. 1991;44(3):221-229.
Kaczmarek, Kurt A. et al.. Electrotactile and Vibrotactile Displays for Sensory Substitution Systems. IEEE Trans. Biomed. Eng. Jan. 1991;38 (1):1-16.
Kantor G et al., The effects of selected stimulus waveforms on pulse and phase characteristics at sensory and motor thresholds, Physical Therapy, 1994, vol. 74(10): 951-962.
Keller, Thierry et al., Electrodes for transcutaneous (surface) electrical stimulation. J. Automatic Control, University of Belgrade. 2008;18(2):35-45.
Koumans, A. J. R. et al., Electrodermal Levels and Fluctuations During Normal Sleep, Psychophysiology, 1968, 5(3), p. 300-306.
Kripke, D.F. et al., Wrist Actigraphic Scoring for Sleep Laboratory Patients: Algorithm Development, Journal of Sleep Research, 2010, 19(4), p. 612-619.
Law PPW et al., Optimal stimulation frequency of transcutaneous electrical nerve stimulation on people with knee osteoarthritis, J Rehabil Med, 2004, vol. 36: 220-225.
Leonard G et al., Deciphering the role of endogenous opioids in high-frequency TENS using low and high doses of naloxone, Pain, 2010, vol. 151: 215-219.
Levy et al., A comparison of two methods for measuring thermal thresholds in diabetic neuropathy, Journal of Neurology, Neurosurgery, and Psychiatry, 1989, vol. 52: 1072-1077.
Lykken, D.T., Properties of Electrodes Used in Electrodermal Measurement. J. Comp. Physiol. Psychol. Oct. 1959;52:629-634.
Lykken, D.T., Square-Wave Analysis of Skin Impedance. Psychophysiology. Sep. 1970;7(2):262-275.
Melzack R et al., Pain mechanisms: A New Theory, Science, 1965, vol. 150(3699): 971-979.
Moran F et al., Hypoalgesia in response to transcutaneous electrical nerve stimulation (TENS) depends on stimulation intensity, The Journal of Pain, 2011, vol. 12(8): 929-935.
Oosterhof, Jan et al., Outcome of transcutaneous electrical nerve stimulation in chronic pain: short-term results of a double-blind, randomised, placebo-controlled trial. J. Headache Pain. Sep. 2006;7(4):196-205.
Oosterhof, Jan et al., The long-term outcome of transcutaneous electrical nerve stimulation in the treatment for patients with chronic pain: a randomized, placebo-controlled trial. Pain Pract. Sep. 2012;12(7):513-522.
Pantaleao MA et al., Adjusting pulse amplitude during transcutaneous electrical nerve stimulation (TENS) application produces greater hypoalgesia, The Journal of Pain, 2011, vol. 12(5): 581-590.
Paquet, J. et al., Wake Detection Capacity of Actigraphy During Sleep, Sleep, 2007, 30(10), p. 1362-1369.
Pieber K et al., Electrotherapy for the treatment of painful diabetic peripheral neuropathy: a review, Journal of Rehabilitation Medicine, 2010, vol. 42: 289-295.
Raskin, J. et al., A Double-Blind, Randomized Multicenter Trial Comparing Duloxetine with Placebo in the Management of Diabetic Peripheral Neuropathic Pain, Pain Medicine, 2005, 6(5), p. 346-356.
Sadeh, A., The Role and Validity of Actigraphy in Sleep Medicine: An Update, Sleep Medicine Reviews, 2011, vol. 15, p. 259-267.
Sadosky, A. et al., Burden of illness Associated with Painful Diabetic Peripheral Neuropathy Among Adults Seeking Treatment in the US: Results from a Retrospective Chart Review and Cross-Sectional Survey, Diabetes, Metabolic Syndrome and Obesity: Targets and Therapy, 2013, vol. 6, p. 79-92.
Scherder, E. J. A. et al., Transcutaneous Electrical Nerve Stimulation (TENS) Improves the Rest-Activity Rhythm in Midstage Alzheimer's Disease, Behavioral Brain Research, 1999, vol. 101, p. 105-107.
Tryon, W. W., Issues of Validity in Actigraphic Sleep Assessment, Sleep, 2004, 27(1), p. 158-165.

(56) References Cited

OTHER PUBLICATIONS

Tsai, Y. et al., Impact of Subjective Sleep Quality on Glycemic Control in Type 2 Diabetes Mellitus, Family Practice, 2012, vol. 29, p. 30-35.
Van Boxtel, A., Skin resistance during square-wave electrical pulses of 1 to 10 mA. Med. Biol. Eng. Comput. Nov. 1977:15(6):679-687.
Van Someren, E. J. W. et al., Gravitational Artefact in Frequency Spectra of Movement Acceleration: Implications for Actigraphy in Young and Elderly Subjects, Journal of Neuroscience Methods, 1996, vol. 65, p. 55-62.
Webster, J. B. et al., An Activity-Based Sleep Monitor System for Ambulatory Use, Sleep, 1982, 5(4), p. 389-399.
Zelman, D. C. et al., Sleep Impairment in Patients With Painful Diabetic Peripheral Neuropathy, The Clinical Journal of Pain, 2006, 22(8), p. 681-685.
Aurora, R. et al., The Treatment of Restless Legs Syndrome and Periodic Limb Movement Disorder in Adults—An Update for 2012: Practice Parameters with an Evidence-Based Systematic Review and Meta-Analyses, Sleep, 2012, vol. 35, No. 8, p. 1039-1062.
Bonnet, M, et al., Recording and Scoring Leg Movements, Sleep, 1993, vol. 16, No. 8, p. 748-759.
Boyle, J. et al., Randomized, Placebo-Controlled Comparison of Amitriptyline, Duloxetine, and Pregabalin in Patients With Chronic Diabetic Peripheral Neuropathic Pain, Diabetes Care, 2012, vol. 35, p. 2451-2458.
Kovacevic-Ristanovic, R. et al., Nonpharmacologic Treatment of Periodic Leg Movements in Sleep, Arch. Phys. Med. Rehabil., 1991, vol. 72, p. 385-389.
Lopes, L. et al., Restless Legs Syndrome and Quality of Sleep in Type 2 Diabetes, Diabetes Care, 2005, vol. 28, No. 11, p. 2633-2636.
Nightingale, S., The neuropathic pain market, Nature Reviews, 2012, vol. 11, p. 101-102.
Zucconi, M. et al., The official World Association of Sleep Medicine (WASM) standards for recording and scoring periodic leg movements in sleep (PLMS) and wakefulness (PLMW) developed in collaboration with a task force from the International Restless Legs Syndrome Study Group (IRLSSG), Sleep Medicine, 2006, vol. 7, p. 175-183.

\* cited by examiner

TRANSCUTANEOUS ELECTRICAL NERVE STIMULATOR WITH AUTOMATIC DETECTION OF LEG ORIENTATION AND LEG MOTION FOR ENHANCED SLEEP ANALYSIS, INCLUDING ENHANCED TRANSCUTANEOUS ELECTRICAL NERVE STIMULATION (TENS) USING THE SAME

REFERENCE TO PENDING PRIOR PATENT APPLICATIONS

This patent application:
(1) is a continuation-in-part of pending prior U.S. Patent Application Publication No. 2015/0306387, filed Jul. 8, 2015 by NeuroMetrix, Inc. and Xuan Kong et al. for MEASURING THE "ON-SKIN" TIME OF A TRANSCUTANEOUS ELECTRICAL NERVE STIMULATOR (TENS) DEVICE IN ORDER TO MINIMIZE SKIN IRRITATION DUE TO EXCESSIVE UNINTERRUPTED WEARING OF THE SAME, which patent application:
(A) is a continuation-in-part of pending prior U.S. Patent Application Publication No. 2015/0148865, filed Jan. 30, 2015 by NeuroMetrix, Inc. and Shai N. Gozani et al. for APPARATUS AND METHOD FOR RELIEVING PAIN USING TRANSCUTANEOUS ELECTRICAL NERVE STIMULATION, which patent application:
  (i) is a continuation of prior U.S. Pat. No. 8,948,876, filed Nov. 15, 2012 by NeuroMetrix, Inc. and Shai N. Gozani et al. for APPARATUS AND METHOD FOR RELIEVING PAIN USING TRANSCUTANEOUS ELECTRICAL NERVE STIMULATION, which patent application claims benefit of:
    (a) prior U.S. Provisional Patent Application Ser. No. 61/560,029, filed Nov. 15, 2011 by Shai N. Gozani for SENSUS OPERATING MODEL; and
    (b) prior U.S. Provisional Patent Application Ser. No. 61/657,382, filed Jun. 8, 2012 by Shai N. Gozani et al. for APPARATUS AND METHOD FOR RELIEVING PAIN USING TRANSCUTANEOUS ELECTRICAL NERVE STIMULATION;
(B) is a continuation-in-part of pending prior U.S. Patent Application Publication No. 2014/0296935, filed May 5, 2014 by NeuroMetrix, Inc. and Thomas Ferree et al. for TRANSCUTANEOUS ELECTRICAL NERVE STIMULATOR WITH USER GESTURE DETECTOR AND ELECTRODE-SKIN CONTACT DETECTOR, WITH TRANSIENT MOTION DETECTOR FOR INCREASING THE ACCURACY OF THE SAME, which patent application:
  (i) is a continuation-in-part of pending prior U.S. Patent Application Publication No. 2014/0296934, filed Mar. 31, 2014 by Neurometrix, Inc. and Shai Gozani et al. for DETECTING CUTANEOUS ELECTRODE PEELING USING ELECTRODE-SKIN IMPEDANCE, which claims benefit of:
    (a) prior U.S. Provisional Patent Application Ser. No. 61/806,481, filed Mar. 29, 2013 by Shai Gozani for DETECTING ELECTRODE PEELING BY RELATIVE CHANGES IN SKIN-ELECTRODE IMPEDANCE;
  (ii) is a continuation-in-part of pending prior U.S. Patent Application Publication No. 2014/0309709, filed Apr. 15, 2014 by Neurometrix, Inc. and Shai Gozani et al. for TRANSCUTANEOUS ELECTRICAL NERVE STIMULATOR WITH AUTOMATIC DETECTION OF USER SLEEP-WAKE STATE, which claims benefit of:
    (a) prior U.S. Provisional Patent Application Ser. No. 61/811,864, filed Apr. 15, 2013 by Shai Gozani for TRANSCUTANEOUS ELECTRICAL NERVE STIMULATOR WITH AUTOMATIC DETECTION OF PATIENT SLEEP-WAKE STATE;
  (iii) claims benefit of prior U.S. Provisional Patent Application Ser. No. 61/819,159, filed May 3, 2013 by Neurometrix, Inc. and Thomas Ferree et al. for TAP DETECTOR WITH HIGH SENSITIVITY AND SPECIFICITY FOR A WEARABLE TRANSCUTANEOUS ELECTRICAL NERVE STIMULATOR; and
  (iv) claims benefit of prior U.S. Provisional Patent Application Ser. No. 61/858,150, filed Jul. 25, 2013 by Neurometrix, Inc. and Andres Aguirre et al. for MOVEMENT REGULATED TRIP CONDITIONS IN A WEARABLE TRANSCUTANEOUS ELECTRICAL NERVE STIMULATOR;
(C) claims benefit of prior U.S. Provisional Patent Application Ser. No. 62/021,807, filed Jul. 8, 2014 by Neurometrix, Inc. and Xuan Kong et al. for MEASURING TENS DEVICE ON-SKIN TIME TO PREVENT AND MINIMIZE SKIN IRRITATION;
(2) claims benefit of prior U.S. Provisional Patent Application Ser. No. 62/213,978, filed Sep. 3, 2015 by Neurometrix, Inc. and Thomas Ferree et al. for TRANSCUTANEOUS ELECTRICAL NERVE STIMULATOR WITH AUTOMATIC DETECTION OF LEG ORIENTATION AND ROTATION FOR ENHANCED SLEEP ANALYSIS; and
(3) claims benefit of prior U.S. Provisional Patent Application Ser. No. 62/01,029, filed Jan. 8, 2015 by Neurometrix, Inc. and Shai Gozani et al. for METHOD AND APPARATUS FOR USING TRANSCUTANEOUS ELECTRICAL NERVE STIMULATION TO AID SLEEP.

The fifteen (15) above-identified patent applications are hereby incorporated herein by reference.

FIELD OF THE INVENTION

This invention relates generally to Transcutaneous Electrical Nerve Stimulation (TENS) devices that deliver electrical currents across the intact skin of a user via electrodes so as to provide symptomatic relief of pain. More specifically, this invention relates to a TENS device worn during sleep, and a method for making novel measurements that broaden and enhance sleep analysis, and includes enhanced transcutaneous electrical nerve stimulation (TENS) using the same.

BACKGROUND OF THE INVENTION

Chronic pain due to diabetic neuropathy and other causes can interfere with sleep, which carries a host of secondary complications. Transcutaneous electrical nerve stimulation (TENS) devices provide pain relief by stimulating sensory nerves, which leads to an increase in endogenous opioids and down-regulation of pain signal transmission to the brain.

A TENS device which could be used during sleep would offer unique opportunities to provide pain relief during bedtime with the goal of improving sleep (see, for example, Barbarisi M, Pace M C, Passavanti M B, et al. Pregabalin and transcutaneous electrical nerve stimulation for postherpetic neuralgia treatment. *Clin J Pain*. September 2010; 26(7):567-572).

However, most TENS devices are designed to operate exclusively during the day (i.e., wake state) without any nighttime (i.e., sleep state) operation. This limitation is evident in the design of conventional TENS devices, in which the electric current is delivered through wires (called leads) that are connected to electrode pads on the skin. Such a design is not practical or safe for use during sleep because the leads are cumbersome and may get tangled or pulled, and because the electrode pads can potentially peel off the skin (which will terminate TENS therapy) or, perhaps worse, can potentially partially peel off the skin, leading to increased current density and negative consequences for the user (e.g., discomfort or, in extreme cases, burns).

In pending prior U.S. patent application Ser. No. 14/230,648, filed Mar. 31, 2014 by NeuroMetrix, Inc. and Shai Gozani et al. for DETECTING CUTANEOUS ELECTRODE PEELING USING ELECTRODE-SKIN IMPEDANCE, published as U.S. Patent Application Publication No. US 2014/0296934 A1 on Oct. 2, 2014, which patent application is hereby incorporated herein by reference, there is disclosed a novel TENS device which allows TENS therapy to be applied during nighttime (i.e., during sleep state) as well as during the day (i.e., wake state). The key design elements that make this novel TENS device suitable for use during sleep are (1) the leads are eliminated because the electrode pads are attached directly to the housing containing the TENS stimulation circuitry, (2) the TENS housing and electrode pads are held reliably and comfortably against the skin by an adjustable strap or band, (3) the TENS device continuously measures skin-electrode contact impedance (and related electrical parameters) so as to detect if the electrode pads peel (completely or partially) off the skin and the TENS device stops delivering current if peeling is detected, (4) therapeutic stimulation may be scheduled in one-hour on-off blocks so as to provide pain relief throughout the night, and (5) the TENS device detects when the user is asleep and reduces the therapeutic stimulation level automatically so as not to disturb sleep.

The novel TENS device disclosed in pending prior U.S. patent application Ser. No. 14/230,648 (and published as U.S. Patent Application Publication No. US 2014/0296934 A1) is designed to be located on the upper calf of the user. This is for three reasons. First, the TENS device needs to stimulate sensory nerve fibers in order to provide widespread pain relief through the systemic effect of an increase in endogenous opioids and down-regulation of pain signal transmission. The upper calf area has a cluster of sensory nerve fibers that can be activated easily with a transcutaneous electrical nerve stimulator because of their proximity to the surface of the skin. Second, some forms of chronic pain (such as that due to diabetic neuropathy) are experienced most acutely in the feet, and in addition to the mechanism of pain suppression through endogenous opioids described above (which is systemic), there is also evidence for additional mechanisms of pain suppression that are more local, thus making it advantageous to place the TENS device on the upper calf of the user. Third, chronic pain can be persistent throughout the day, often worsening at night, and wearing the TENS device on the upper calf makes it discreet and unobtrusive, which encourages more regular use.

As mentioned above, the novel TENS device disclosed in pending prior U.S. patent application Ser. No. 14/230,648 (and published as U.S. Patent Application Publication No. US 2014/0296934 A1), which is designed for use during sleep, detects when the user is asleep and adjusts the therapeutic stimulation level to avoid disturbing sleep. It would be advantageous for a TENS device aimed at improving sleep quality to also quantify sleep quality and sleep disorders, since users will be more likely to use the TENS device if they are aware of, and convinced of, its benefit to their sleep.

The gold standard in determining the sleep-wake state of a subject is polysomnography which comprises at least three distinct types of data, i.e., electroencephalogram (EEG), electrooculography (EOG) and electromyography (EMG). Because of the difficulty in recording and analyzing these types of data, actigraphy has been developed and refined over the last 30 years as a practical alternative to study sleep/awake patterns. Actigraphy is a continuous recording of body movement by means of a body-worn device, typically equipped with accelerometers [Ancoli-Israel S, Cole R, Alessi C, Chambers M, Moorcroft W, Pollak C P. The role of actigraphy in the study of sleep and circadian rhythms. *Sleep. May* 1 2003; 26(3):342-392].

Wearable electronic devices for health and fitness have become widespread, and most have accelerometers and, from acceleration data, compute various metrics of activity either to track daytime activities or to quantify sleep patterns. Most of these actigraphy-based devices are worn on the wrist however, and in certain ways that limits their ability to detect and quantify sleep.

SUMMARY OF THE INVENTION

Significantly, it has now been recognized that the placement of a novel, accelerometer-equipped TENS device on the upper calf, with tight mechanical coupling to the upper calf, may be used to support novel approaches for detecting when the user is asleep, and novel metrics for analyzing the sleep of the user, and novel approaches to quantify body and leg motions associated with poor sleep quality and/or disorders such as restless leg syndrome, and novel approaches for providing enhanced transcutaneous electrical nerve stimulation (TENS) using the same. Among these novel metrics are "leg movements", "body roll events" associated with rolling over in bed, and "time-on-back" which is relevant to users suffering not only from chronic pain but also from problematic sleep positions which can cause snoring or sleep apnea. In addition to tracking and reporting sleep indicators, real-time feedback to the user based on indicator trends can also help the user to improve sleep quality. An example is to provide an alert (via mechanical or electrical means, for example) to the user when time-on-back duration exceeds a threshold. Another example is to alter TENS stimulation parameters when leg movement patterns associated with discomfort caused by nighttime pain are detected in order to enhance the analgesic effect of TENS therapy.

Thus, the present invention comprises the provision and use of a novel TENS device which comprises a TENS stimulator designed to be placed on the user's upper calf and a pre-configured electrode array designed to provide circumferential stimulation to the upper calf of the user. A three-axis (x, y, z) accelerometer incorporated in the TENS device continuously measures the projection of static gravity onto each axis (i.e., x, y, z), which depends on the device orientation, and time-varying acceleration on each axis due to user motion along that axis.

The placement of the novel TENS device on the upper calf of the user is used to support novel approaches for detecting when the user is asleep, and for quantifying sleep and assessing abnormal body and leg motions, and for providing enhanced TENS therapy using such sleep analysis.

First, the novel TENS device measures leg orientation, which is highly correlated with body orientation and therefore indicative of the user's recumbent state (and thereby the user's sleep-wake state). Specifically, the novel TENS device measures two distinct aspects of leg orientation: leg "elevation" (or the angle of the lower leg relative to the horizontal), and leg "rotation" (or the angle of rotation of the lower leg about its own axis).

Second, the novel TENS device measures leg motion, which is also indicative of the user's sleep-wake state. Specifically, the novel TENS device measures two distinct aspects of leg motion: "net activity" (which is the magnitude of movement-related acceleration averaged within one-minute windows), and "leg movements" (or brief events that are known to occur in sleep but are not evident in net activity). Some leg movements accompanied by a large leg rotation may be further classified as "body roll events" (such as occur when rolling over in bed). Repetitive leg movements may occur in people with chronic pain and other medical conditions, and may degrade the quality of sleep experienced by the person (and his/her sleep partner). Quantification and monitoring of the repetitive leg movements may provide insights to these conditions and trends of these conditions.

Third, the novel TENS device combines these two measures of leg orientation (i.e., leg elevation and leg rotation) and two measures of leg motion (i.e., net activity and leg movements) to improve sleep quantification and to utilize more precise quantification metrics to enhance therapeutic benefits.

The determination of sleep-wake state by the novel TENS device proceeds in several steps. The user is considered to be "in-bed" if the user's leg orientation is determined to be recumbent (i.e., near horizontal) for a selected portion (e.g., a majority) of a selected time period (e.g., a decision window). During the in-bed state, "sleep onset" is defined as the first time that the user's net activity and leg movements fall below set thresholds for a specified period of time (e.g., a decision window). Following sleep onset, the novel TENS device measures net activity and leg movements. During all of the time intervals in which the net activity is below some specified threshold, the user is considered to be "asleep". During all of the time in which the user is recumbent, the net activity is below some net activity threshold, the number of leg movements is below some leg movement threshold, and the number of body rolls is zero, the user is considered to be "restful". During all of the time in which the static leg rotational angle falls between two static leg rotational angle thresholds, the user is considered to be sleeping "on-back". These times, and the ratios of these times, may be used to compute measures of "sleep duration" and "sleep quality". This sleep analysis may then be reported (e.g., to the user and/or to the care provider of the user) and/or used to provide enhanced TENS therapy to the patient.

In one preferred form of the present invention, there is provided apparatus for providing transcutaneous electrical nerve stimulation (TENS) therapy to a user, said apparatus comprising:

a housing;

an application unit for providing mechanical coupling between said housing and the user's body;

a stimulation unit for electrically stimulating at least one nerve of the user;

a sensing unit for sensing the user's body movement and body orientation; and a reporting unit for providing the user with feedback based on the user's sensed body movement and body orientation.

In another preferred form of the present invention, there is provided a method for applying transcutaneous electrical nerve stimulation to a user, said method comprising the steps of:

applying a stimulation unit and a sensing unit to the user's body;

using the stimulation unit to deliver electrical stimulation to the user to stimulate one or more nerves;

analyzing electromechanical sensing data from the sensing unit to quantify the user's body orientation and body activity levels; and modifying the electrical stimulation delivered by the stimulation unit based on the user's body orientation and body activity levels.

In another preferred form of the present invention, there is provided apparatus for monitoring the sleep patterns of a user, said apparatus comprising:

a housing;

an application unit for providing mechanical coupling between said housing and the user's body;

a sensing unit disposed within the housing to sense the user's body movement and body orientation; and a reporting unit for providing the user with feedback based on the user's sensed body movement and body orientation.

In another preferred form of the present invention, there is provided a method for monitoring the sleep patterns of a user, said method comprising of the steps of:

applying a sensing unit and a feedback unit to the user body;

using the sensing unit to determine the user's body movement and body orientation; and providing the user with feedback via said feedback unit based on body activity and body orientation.

In another preferred form of the present invention, there is provided apparatus for providing transcutaneous electrical nerve stimulation (TENS) therapy to a user, said apparatus comprising:

a housing;

an application unit for providing mechanical coupling between said housing and the user's leg;

a stimulation unit for electrically stimulating at least one nerve of the user; and a sensing unit for sensing the user's leg orientation and leg motion, wherein sensing the user's leg orientation comprises determining the user's leg elevation and leg rotation, and further wherein sensing the user's leg motion comprises determining the user's net activity and leg movements; and a controller for modulating said stimulation unit based on the determinations made by said sensing unit.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

The Novel TENS Device In General

Figure 1:
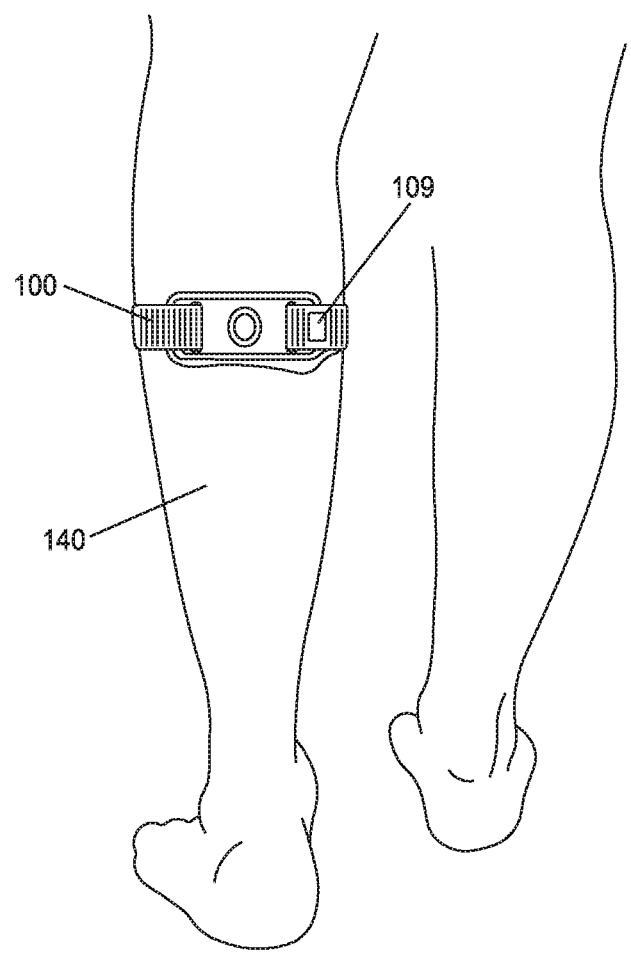
FIG. 1 is a schematic view showing a novel TENS device formed in accordance with the present invention, with the novel TENS device being mounted to the upper calf of a user.

FIG. 1 illustrates a novel TENS device 100 formed in accordance with the present invention, with the novel TENS device being shown worn on a user's upper calf 140. A user may wear TENS device 100 on either leg.

Figure 2:
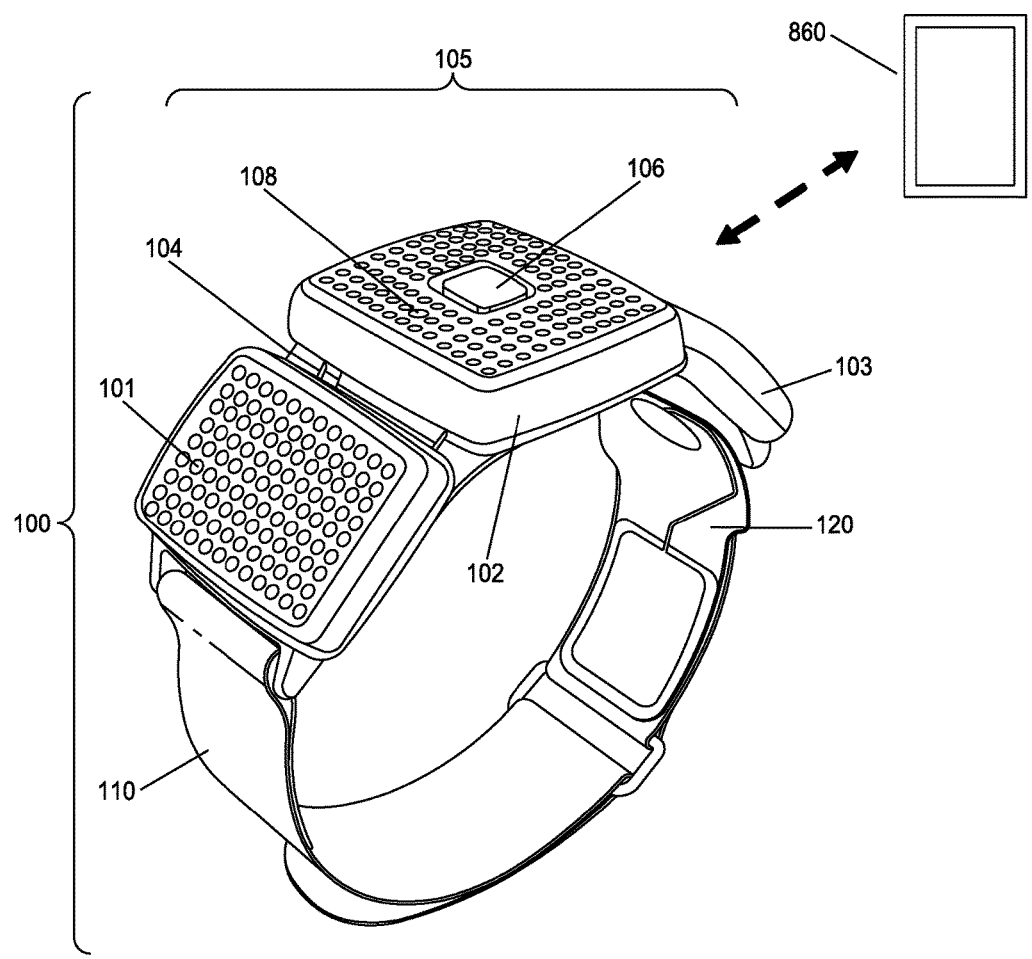
FIG. 2 is a schematic view showing the novel TENS device of FIG. 1 in greater detail.
Figure 4:
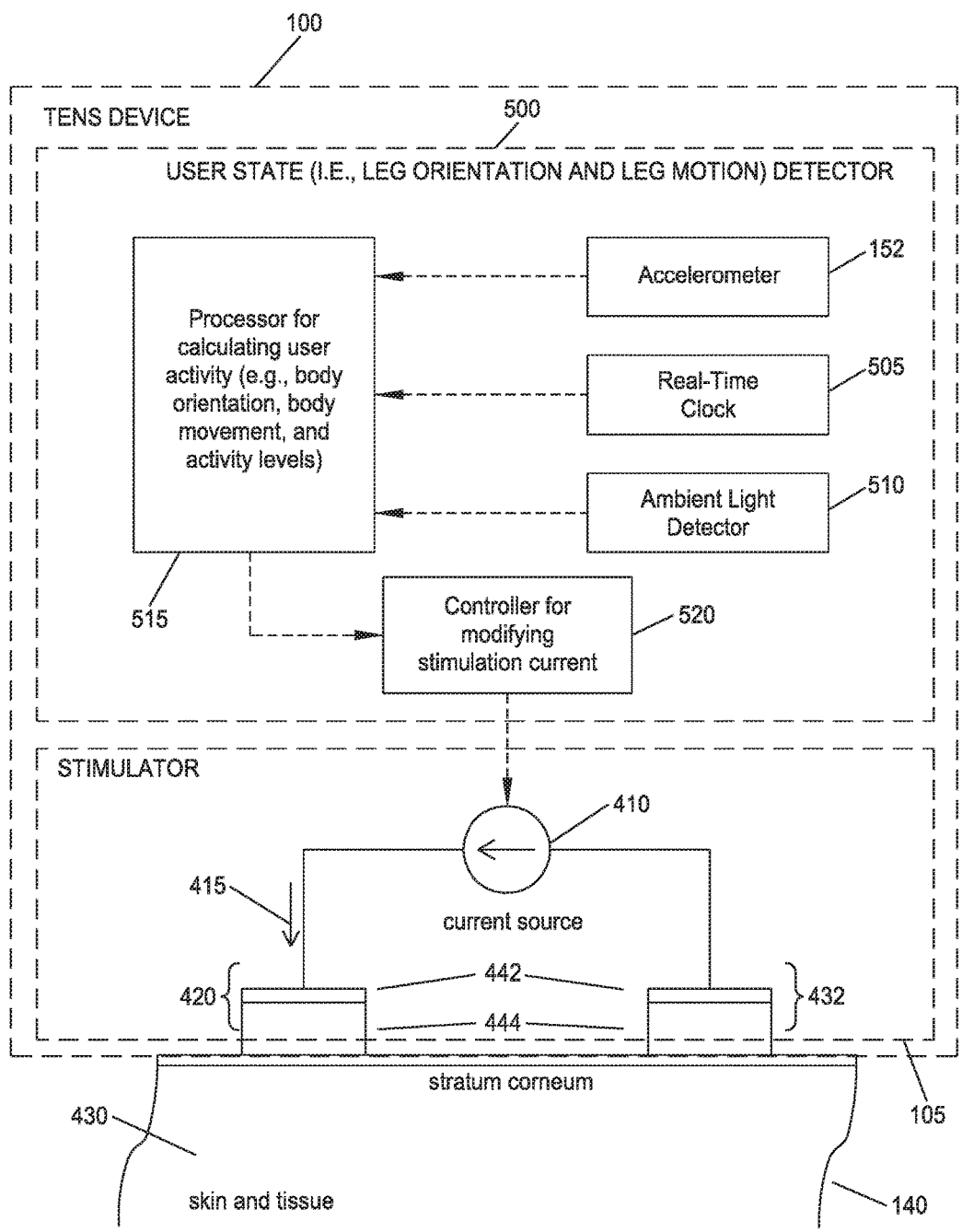
FIG. 4 is a schematic view of the novel TENS device of FIGS. 1 and 2, including its user state (i.e., leg orientation and leg motion) detector.
Figure 6:
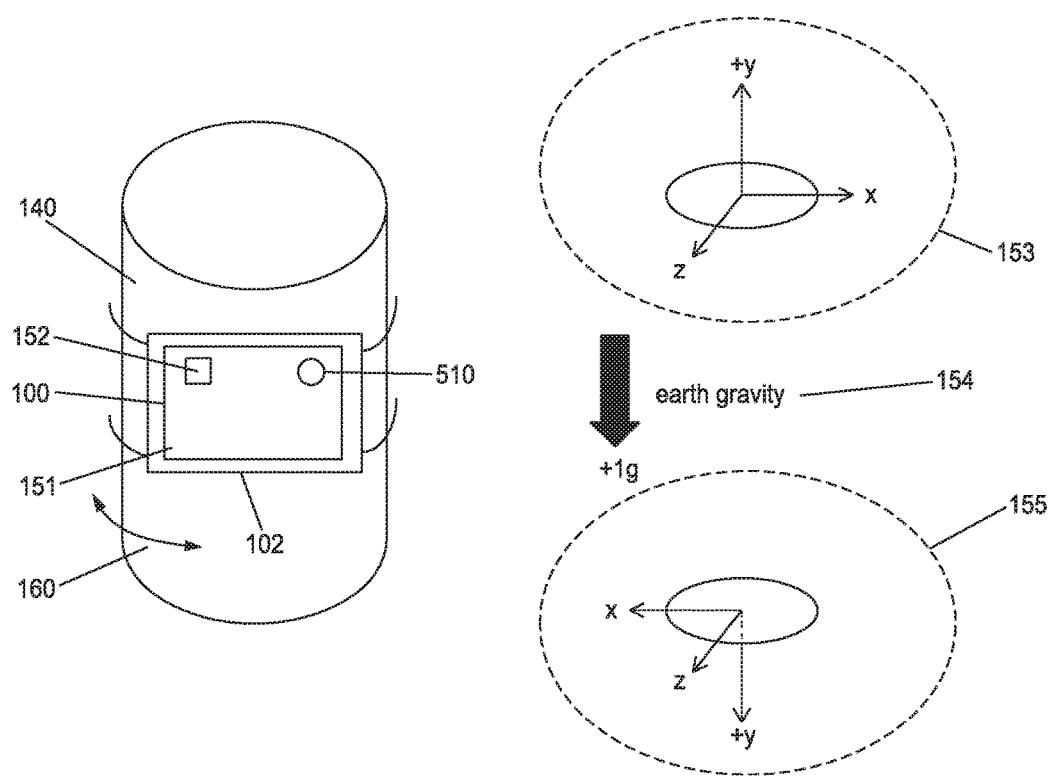
FIG. 6 is a schematic view showing the orientation of the accelerometer incorporated in the novel TENS device of FIGS. 1 and 2, when the novel TENS device of FIG. 1 is applied to the upper calf of a user.

TENS device 100 is shown in greater detail in FIG. 2 and preferably comprises three primary components: a stimulator 105, a strap 110, and an electrode array 120 (comprising a cathode electrode and an anode electrode appropriately connected to stimulator 105 as is well known in the art). Stimulator 105 preferably comprises three mechanically and electrically inter-connected compartments 101, 102, and 103. Compartments 101, 102, 103 are preferably inter-connected by hinge mechanisms 104 (only one of which is shown in FIG. 2), thereby allowing TENS device 100 to conform to the curved anatomy of a user's leg. In a preferred embodiment of the present invention, compartment 102 houses the TENS stimulation circuitry (except for a battery) and user interface elements 106 and 108. Compartment 102 also houses an accelerometer 152 (see FIGS. 4 and 6), preferably in the form of a semiconductor chip accelerometer, for detecting user gestures, user leg and body orientation, and user leg and body motion, as will hereinafter be discussed. Compartment 102 also houses a real-time clock 505 (FIG. 4). In a preferred embodiment, compartments 101 and 103 are smaller, auxiliary compartments that house a battery for powering the TENS stimulation circuitry and other circuitry, and other ancillary elements, such as an ambient light sensor or detector 510 (FIGS. 4 and 6) for determining ambient light conditions, and a wireless interface unit of the sort well known in the art (not shown) for allowing TENS device 100 to wirelessly communicate with other elements (e.g., a hand-held electronic device such as a smartphone 860). In another embodiment of the present invention, only one or two compartments may be used for housing all of the TENS stimulation circuitry, battery, and other ancillary elements of the present invention. In another embodiment of the present invention, a greater number of compartments are used, e.g., to conform better to the body and to improve user comfort. In another embodiment of the present invention, a flexible circuit board is used to distribute the TENS stimulation circuitry and other circuitry more evenly around the leg and thereby reduce bulk.

Still looking now at FIG. 2, user interface element 106 preferably comprises a push button for user control of electrical stimulation, and user interface element 108 preferably comprises an LED for indicating stimulation status and for providing other information to the user. Additional user interface elements (e.g., a multi-LED array, LCD display, audio feedback through a beeper or voice output, haptic devices such as a vibrating motor, etc.) may also be provided and are considered to be within the scope of the present invention.

The preferred embodiment of the present invention is designed to be worn on the upper calf 140 of the user as shown in FIG. 1. TENS device 100, comprising stimulator 105, electrode array 120, and strap 110, is secured to upper calf 140 by placing the apparatus in position and then tightening strap 110. Although the preferred embodiment of the present invention comprises placement of the TENS device on the upper calf of the user, additional anatomical locations (such as above the knee, on the lower back, and on the upper arm) are also contemplated and are also considered to be within the scope of the present invention.

Figure 3:
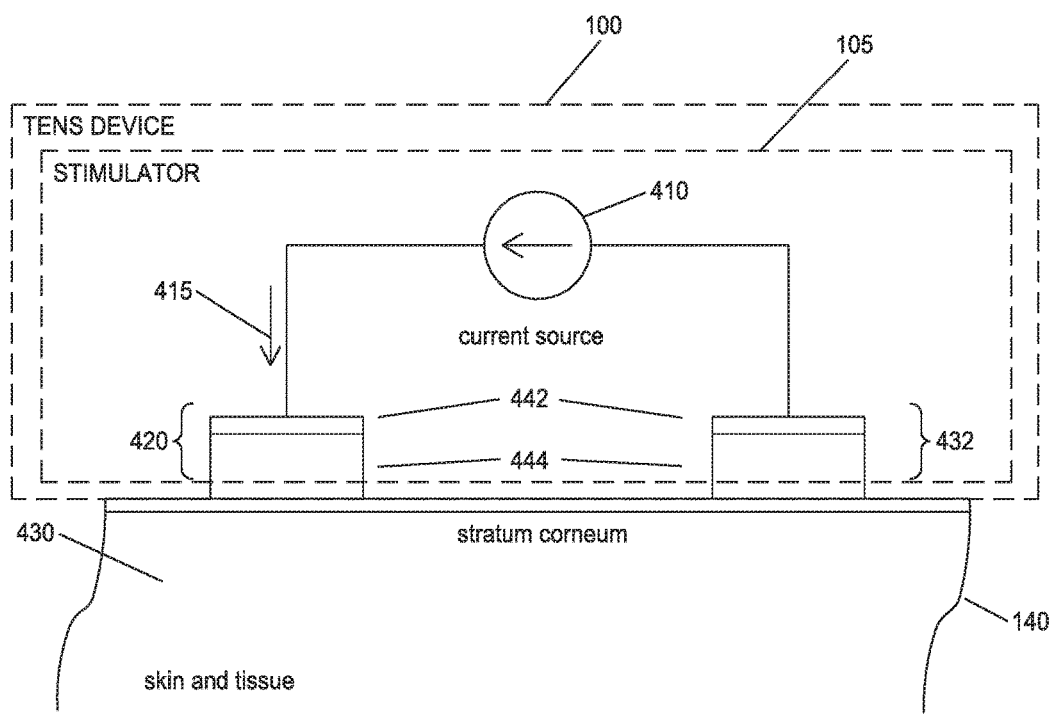
FIG. 3 is a schematic view of the novel TENS device shown in FIGS. 1 and 2 attached to the tissue of a patient.

FIG. 3 is a schematic representation of the current flow between TENS device 100 and the user. As seen in FIG. 3, stimulation current 415 from a constant current source 410 flows into the user's tissue 430 (e.g., the user's upper calf) via anode electrode 420. Anode electrode 420 comprises a conductive backing (e.g., silver hatch) 442 and hydrogel 444. The current passes through the user's tissue 430 and returns to constant current source 410 through cathode electrode 432 (cathode electrode 432 also comprises a conductive backing 442 and hydrogel 444). Constant current source 410 preferably provides an appropriate biphasic waveform (i.e., biphasic stimulation pulses) of the sort well known in the art of TENS therapy. In this respect it should be appreciated that the designation of "anode" and "cathode" electrodes is purely notational in the context of a biphasic waveform (i.e., when the biphasic stimulation pulse reverses its polarity in its second phase of the biphasic TENS stimulation, current will be flowing into the user's body via "cathode" electrode 432 and out of the user's body via "anode" electrode 420).

Further details regarding the construction and use of the foregoing aspects of TENS device 100 are disclosed in (i) U.S. Pat. No. 8,948,876, issued Feb. 3, 2015 to NeuroMetrix, Inc. and Shai N. Gozani et al. for APPARATUS AND METHOD FOR RELIEVING PAIN USING TRANSCUTANEOUS ELECTRICAL NERVE STIMULATION, which patent is hereby incorporated herein by reference, and (ii) pending prior U.S. patent application Ser. No. 14/230,648, filed Mar. 31, 2014 by Shai N. Gozani et al. for DETECTING CUTANEOUS "ELECTRODE PEELING" USING ELECTRODE-SKIN IMPEDANCE, published as U.S. Patent Application Publication No. US 2014/0296934 A1 on Oct. 2, 2014, which patent application is hereby incorporated herein by reference.

The User State (i.e., Leg Orientation And Leg Motion) Detector

In accordance with the present invention, TENS device 100 further comprises (e.g., within compartment 102) user state (i.e., leg orientation and leg motion) detector 500 for (i) determining the sleep-wake state of the user, (ii) analyzing the sleep of the user, and/or (iii) providing enhanced transcutaneous electrical nerve stimulation (TENS) using the same. To this end, and looking now at FIG. 4, user state (i.e., leg orientation and leg motion) detector 500 generally comprises the aforementioned accelerometer 152, the aforementioned real-time clock 505, the aforementioned ambient light detector 510, a processor 515 for calculating user activity (e.g., body orientation, body movement and activity levels), and a controller 520 for modifying the stimulation current provided by the constant current source 410 of TENS device 100 in accordance with determinations made by processor 515.

When the TENS device is secured in position on the user's upper calf, the position and orientation of accelerometer 152 (FIGS. 4 and 6) of TENS device 100 is fixed relative to the lower limb of the user. Tight mechanical coupling between TENS device 100 and lower limb 140 allows movement of the user's lower limb to be accurately measured by accelerometer 152. Such tight mechanical coupling is preferably established through the aforementioned strap 110. Alternatively, tight mechanical coupling may be established through other means, e.g., a flexible band encasing the TENS device. If desired, a tension gauge 109 (FIG. 1) may be provided on strap 110 to confirm that a tight mechanical coupling is established between TENS device 100 and upper calf 140.

Data from accelerometer 152 are analyzed in real time by processor 515 of user state (i.e., leg orientation and leg motion) detector 500 to determine the orientation and motion of the lower limb (i.e., upper calf 140) of the user. The orientation, motion, and activity level of the lower limb (i.e., upper calf 140) of the user, determined by analyzing the data from accelerometer 152, are used to determine the sleep-wake state and sleep patterns of the user. Based on the sleep-wake state and sleep patterns, TENS device 100 can modify its stimulation pattern (such as the stimulation intensity level and the onset of the stimulation) via controller 520, or provide the user with additional feedback (such as mechanical vibration if the duration of the sleep-on-back state exceeds a threshold).

The leg orientation and leg motion components measured by the user state (i.e., leg orientation and leg motion) detector 500 of the present invention may individually or collectively contribute to the determination of the sleep-wake state of the user. In one preferred form of the invention, processor 515 of TENS device 100 measures the calf orientation of the user, which is highly correlated with the body orientation of the user. More particularly, upright body orientation is generally a reliable indicator that the user is in a wake state, while recumbent orientation suggests a resting state (e.g., such as occurs during sleep). Regular and robust body movement is more likely the result of user activities during the daytime (i.e., during wake state), while quiet or low-level spontaneous movements are more likely during nighttime (i.e., during sleep state). Interactions of body orientation and movement level can also be useful in identifying the sleep-wake state of the user (i.e., thereby enhancing a sleep-wake state classification). Specifically, recumbent body orientation and a low-level of physical activity is generally a good indicator that the user is asleep.

In addition, real-time clock 505 of user state (i.e., leg orientation and leg motion) detector 500 allows assigning a nontrivial a priori probability of the sleep-wake state at any given time of the day in order to further refine the sleep-wake state classification results obtained by the aforementioned analysis of leg orientation and leg motion data (i.e., a user is more likely to be asleep at 3:00 am and less likely to be asleep at 4:00 pm). In a preferred embodiment of the present invention, to reflect that the a priori probability that the sleep state is low at a specific daytime window, the threshold value for classifying user body orientation as recumbent can be made more stringent.

In another embodiment of the present invention, output from ambient light sensor 510 is used to improve sleep-wake classification results. The ambient light sensor 510 can be used to determine if the user is in an environment which has an illuminated or non-illuminated ambience, to reflect the a priori probability that a user is more likely to be sleeping in a dark setting than in a brightly lit setting. Accordingly, the threshold values for classifying user body position and motion level can be adjusted to reflect the a priori probability of sleep.

On-Skin Detector

In one preferred form of the invention, TENS device 100 may comprise an on-skin detector to confirm that TENS device 100 is firmly seated on the skin of the user.

Figure 5:
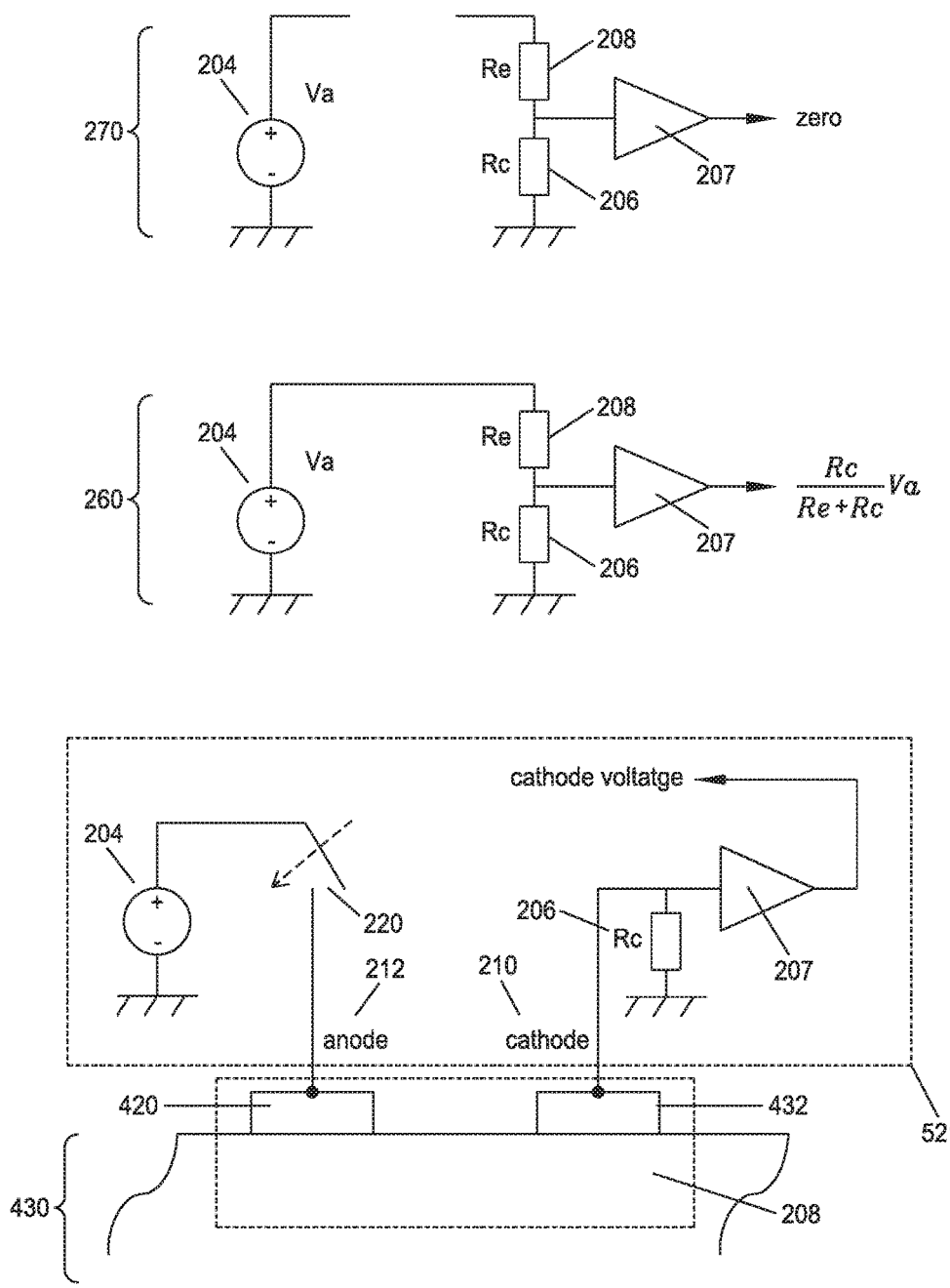
FIG. 5 is a schematic view showing the on-skin detection system of the novel TENS device shown in FIGS. 1 and 2, as well as its equivalent circuits when the novel TENS device is on and off the skin of a user.

More particularly, the orientation and motion measures from accelerometer 152 in TENS device 100 only become coupled with the orientation and motion of a user when the TENS device is worn by the user. In a preferred embodiment, an on-skin detector 521 is provided to determine whether and when TENS device 100 is securely placed on the user's upper calf. In the preferred embodiment, and looking now at FIG. 5, on-skin detector 521 may be provided within TENS device 100. More particularly, in one preferred form of the invention, a voltage of 20 volts from voltage source 204 is applied to the anode terminal 212 of TENS stimulator 105 by closing the switch 220. If the TENS device is worn by the user, then user tissue 430, interposed between anode electrode 420 and cathode electrode 432, will form a closed circuit to apply the voltage to the voltage divider circuit formed by resistors 208 and 206. More particularly, when TENS device 100 is on the skin of the user, the equivalent circuit 260 shown in FIG. 5 represents the real-world system and equivalent circuit 260 allows the anode voltage $V_a$ 204 to be sensed through the voltage divider resistors 206 and 208. The cathode voltage measured from the amplifier 207 will be non-zero and close to the anode voltage 204. On the other hand, when TENS device 100 is not on the skin of the user, the equivalent circuit 270 represents the real-world system and the cathode voltage from amplifier 207 will be zero.

On-skin detector 521 is preferably employed in two ways.

First, if on-skin detector 521 indicates that electrode array 120 of TENS device 100 has become partially or fully detached from the skin of the user, TENS device 100 can stop applying TENS therapy to the user.

Second, if on-skin detector 521 indicates that electrode array 120 of TENS device 100 has become partially or fully detached from the skin of the user, processor 515 of TENS device 100 will recognize that the data from accelerometer 152 may not reliably reflect user leg orientation and leg motion, and user state (i.e., leg orientation and leg motion) detector 500 can take appropriate action (e.g., alert the user). In this respect it should be appreciated that, when the on-skin detector 521 indicates that TENS device 100 is on the skin of the user, and accelerometer 152 is closely coupled to the lower limb of the user, the data from accelerometer 152 may be representative of user leg orientation and user leg motion. However, when the on-skin detector 521 indicates that TENS device 100 is not on the skin of the user, accelerometer 152 is not closely coupled to the lower limb of the user, and the data from accelerometer 152 will not be representative of user leg orientation and user leg motion.

Accelerometer Data Processing

In one preferred form of the invention, user state (i.e., leg orientation and leg motion) detector 500 comprises a processor 515 for taking the accelerometer data from accelerometer 152 and calculating user activity (e.g., body orientation, body movement and activity levels).

More particularly, in one preferred form of the invention, processor 515 uses the accelerometer data from accelerometer 152 to measure the user's leg orientation, which is highly correlated with body orientation and therefore indicative of the user's recumbent state (and thereby the user's sleep-wake state); and processor 515 uses the accelerometer data from accelerometer 152 to measure the user's leg motion, which is also indicative of the user's sleep-wake state and leg motion activity levels; and processor 515 uses the determinations of user leg orientation and user leg motion to enhance sleep quantification.

More particularly, processor 515 uses the accelerometer data from accelerometer 152 to measure two distinct aspects of the user's leg orientation: leg "elevation" (or the angle of the lower leg relative to the horizontal plane), and leg "rotation" (or the angle of rotation of the lower leg about its own axis).

And processor 515 uses the accelerometer data from accelerometer 152 to measure two distinct aspects of leg motion: "net activity" (which is the magnitude of movement-related acceleration averaged within one-minute windows), and "leg movements" (or brief events that are known to occur in sleep but are not evident in net activity). Some leg movements accompanied by a large leg rotation may be further classified as "body roll events" (such as occur when rolling over in bed).

In a preferred embodiment of the present invention, processor 515 for calculating user activity (e.g., body orientation, body movement and activity levels) is constructed and configured to operate as follows. Raw accelerometer data produced at 400 Hz are decimated to 50 Hz. Following that, the time scale of an "instant" is defined to be equal to 0.1 sec. The 50 Hz data on each axis (x, y, z) are separately averaged over each instant, to provide a low-noise data stream at 10 Hz, denoted by $A_x(t)$, $A_y(t)$, and $A_z(t)$.

The accelerometer data $A_x(t)$, $A_y(t)$, and $A_z(t)$ are used to form features which are averages of $A_x(t)$, $A_y(t)$, and $A_z(t)$ over a longer time window (e.g., a one minute window) to capture the steady-state projection of earth gravity along each axis (x, y, z). These features are used for detecting leg orientation (i.e., leg elevation and leg rotation).

Additionally, the accelerometer data $A_x(t)$, $A_y(t)$, and $A_z(t)$ are high-pass filtered to remove the static gravity component in order to isolate acceleration components caused by leg movement. The high-pass filter has −3 dB point at 0.5 Hz. High-pass filtered accelerometer data are denoted as $\tilde{A}_x(t)$, $\tilde{A}_y(t)$, and $\tilde{A}_z(t)$.

Leg Elevation Detection

In one preferred form of the invention, user state (i.e., leg orientation and leg motion) detector 500 is configured to detect leg elevation.

More particularly, in order to determine the "body orientation state" for the purpose of sleep monitoring, the present invention uses the leg elevation, which is computed by processor 515 of user state (i.e., leg orientation and leg motion) detector 500, based on measurement data from accelerometer 152 when TENS device 100 is placed on the user's upper calf 140 (FIG. 1). In a preferred embodiment, and looking now at FIG. 6, accelerometer 152 is located on the circuit board 151 of the TENS circuitry housed inside compartment 102, so that the accelerometer's 3-axis directions, shown at 153 in FIG. 6 (i.e., x-axis, y-axis, z-axis), are known and fixed in relationship to the lower leg when the TENS device is placed on the user's upper calf: the y-axis is aligned longitudinally along the longitudinal axis of the lower leg; the x-axis is disposed tangential to the surface of the lower leg and perpendicular to the y-axis, and the z-axis points radially away from the surface of the lower leg.

A stationary upright user, or one sitting with feet resting on the ground, will have an upright calf elevation. Consequently, the y-axis acceleration of accelerometer 152 will have a value of about −1 g due to Earth gravity 154 (FIG. 6), where g is the acceleration due to Earth gravity. The above measurement holds true regardless of the exact rotational position 160 of compartment 102 around upper calf 140. When TENS device 100 is placed upside down on the upper calf, which is a possible placement position, the accelerometer axes rotate as shown at 155 in FIG. 6. In this case, a stationary upright user will have a measured acceleration value along the y-axis of about +1 g. By contrast, a stationary recumbent user lying with legs elevated on a bed will have a measured acceleration value along the y-axis of about 0 g. In a preferred embodiment, if the absolute value of the y-axis acceleration measurement is greater than a threshold level, then the leg elevation is considered to be upright, otherwise the leg elevation is considered to be recumbent.

Figure 7:
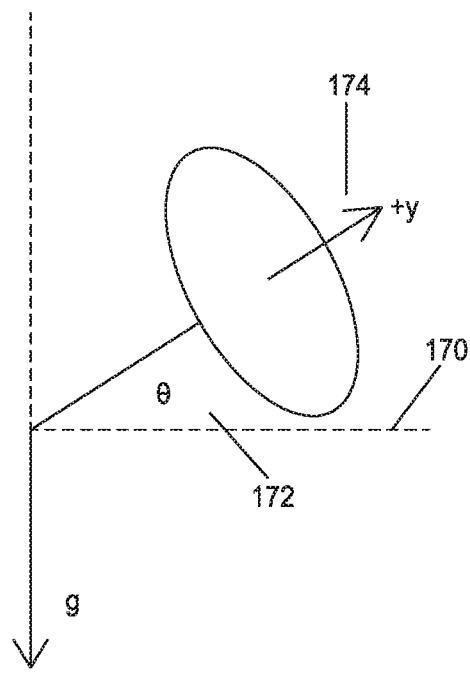
FIG. 7 is a schematic view showing the relationship between gravitational force vector g and the accelerometer y-axis in the novel TENS device when the novel TENS device (applied to upper calf of the user) rests at an elevation angle θ with respect to the horizontal plane.

Looking now at FIG. 7, where the Earth's gravitational vector is downward, the elevation angle θ (172) represents the angle between the positive accelerometer y-axis direction (174) and the true horizontal plane (170). In a preferred embodiment, the y-axis acceleration measurement threshold level is set to 0.50 g, corresponding to a leg elevation angle θ≈30° from the horizontal plane, however, other threshold values may also be used, and users may have the option of adjusting this value to better distinguish their sleep and wake behaviors.

In general, the acceleration measured along the y-axis will include not only the projection of gravity onto that axis, but also a contribution from motion:

$A_y(t) = \pm \sin|\theta(t)| + m(t)$ [in unit of g]

where t is time, and m(t) is the contribution due to leg motion. The specific ±sign depends upon the TENS device placement on upper calf 140 and is fixed for each placement. The motion component m(t) is considered "noise" in the context of determining leg elevation, and will have zero mean over a sufficiently large window.

In a preferred embodiment, a leg elevation algorithm, taking into account user body movement, is implemented by processor 515 of user state (i.e., leg orientation and leg motion) detector 500 in the following manner.

Step 1. Set a target angle threshold $\theta_0$ (this is the "Threshold1" shown at step 910 in FIG. 10) for the angle $\theta$ so that $|\theta|<\theta_0$ corresponds to the case where the upper calf 140 of the user is recumbent. In a preferred embodiment, the target angle threshold $\theta_0$ is set to 30°.

Step 2. Define non-overlapping windows of length N, called "epochs". The time at the end of each epoch is denoted T. In a preferred embodiment, the accelerometer data (in units of g, standard earth gravity) are segmented into epochs, i.e., one-minute windows. With an accelerometer data rate of 10 Hz, the epoch length is N=600. The mean $A_{y,T}$ and the standard error of the mean $SE_{Y,T}$ are calculated based on samples in each epoch.

Step 3. Let $\theta_T = \sin^{-1} A_{y,T}$. Values of $\theta_T \approx \theta_0$ can lead to erratic switching of the leg elevation state. In order to reduce this, define a hysteresis band $\theta_0 \pm \theta_H$. In the preferred embodiment, the hysteresis parameter $\theta_H$ is set to 2.5°, but other values are possible (but should be small compared to $\theta_0$). In the preferred embodiment, rather than computing $\sin^{-1}$ for every epoch, the angular thresholds are instead converted to acceleration units, i.e., by computing two thresholds $A_\pm = \sin(\theta_0 \pm \theta_H)$, against which $A_{y,T}$ will be compared.

Step 4. The ability of the hysteresis band to prevent erratic switching of the leg elevation state depends upon the amount of noise in the data, characterized by $SE_{Y,T}$, which is the standard error of the mean $A_{y,T}$. In order to account for the noise level in the data, processor 515 of user state (i.e., leg orientation and leg motion) detector 500, processor 515 compares the acceleration data $A_{y,T}$ to the thresholds $A_\pm$. However, instead of comparing the mean $A_{y,T}$ per se to the thresholds $A_\pm$, processor 515 compares the "confidence interval" $A_{y,T} \pm \eta SE_{Y,T}$ to the thresholds $A_\pm$. More specifically, for each epoch, if the prior elevation state was recumbent, in order to classify the next state as upright, processor 515 of user state (i.e., leg orientation and leg motion) detector 500 requires $[|A_{y,T}|-\eta SE_{Y,T}]>A_+$. If the prior elevation state was upright, in order to classify the next state as recumbent, processor 515 of user state (i.e., leg orientation and leg motion) detector 500 requires $[|A_{y,T}|+\eta SE_{Y,T}]<A_-$. In a preferred embodiment $\eta=3$, but other values are possible.

Instantaneous Activity

In one preferred form of the invention, processor 515 of user state (i.e., leg orientation and leg motion) detector 500 may be configured to detect instantaneous activity.

More particularly, when TENS device 100 is worn on the user's upper calf 140, the user's activity will be captured by accelerometer 152 of the TENS device. Each axis (x, y, z) of accelerometer 152 measures the projection of the acceleration vector along that axis. As described above, the measured acceleration includes the static effect of earth gravity, as well as contributions from leg movement. In order to isolate the contributions from leg movement, processor 515 of user state (i.e., leg orientation and leg motion) detector 500 high-pass filters the instant data vector $A(t)=[A_x(t), A_y(t), A_z(t)]$ before further processing.

Although the acceleration component for each individual axis of the accelerometer contains unique and useful information for body movement analysis, the vector magnitude of acceleration, called the "instantaneous acceleration", denoted $\tilde{A}_I(t)$ and defined in equation below, is commonly used to quantify the overall motion-related activity:

$$\tilde{A}_I(t) \sqrt{\tilde{A}_X(t)^2 + \tilde{A}_Y(t)^2 + \tilde{A}_Z(t)^2}$$

In a preferred embodiment of the present invention, processor 515 of user state (i.e., leg orientation and leg motion) detector 500 uses this instantaneous acceleration $\tilde{A}_I(t)$ for the actigraphy calculations. However, calculations based on other combinations of acceleration axes may also be used. For example, rather than combining all three axes equally as done with $\tilde{A}_I(t)$ as defined above, only some axes may be used, or certain axes may be contrasted through subtraction.

Leg Movement Detector

In one preferred form of the invention, processor 515 of user state (i.e., leg orientation and leg motion) detector 500 may be configured to detect leg movement.

More particularly, the instantaneous acceleration $\tilde{A}_I(t)$ is a time series comprised of brief events, such as leg movements known to occur during normal and abnormal sleep, and sustained activity, such as occurs during walking, running, or climbing stairs. In a preferred embodiment, leg movements (LM) are computed in a manner that is consistent with the detection of periodic leg movements (PLM) defined in the clinical literature (Bonnet et al, 1993; Zucconi et al, 2006), however, other approaches to detecting brief leg movements are possible and are considered to be within the scope of the present invention.

In the preferred embodiment, a leg movement (LM) detection algorithm is implemented by processor 515 of user state (i.e., leg orientation and leg motion) detector 500 in the following manner.

Step 1. Define two thresholds (these are the "Threshold2" and "Threshold3" shown at steps 914 and 918, respectively, in FIG. 10) that through data analysis are found to be sensitive and specific to brief leg movements. In the preferred embodiment, and appropriate to the variance properties of the data measured by the accelerometer 152, these thresholds are 0.02 g (816 in FIGS. 8) and 0.03 g (815 in FIG. 8), but other values may also be used.

Step 2. Define an instantaneous activity state (IAS) and initialize the IAS to False.

Step 3. Compute instantaneous acceleration $\tilde{A}_I(t)$ for each time instant.

Step 3. Update the IAS for each time instant as follows. If IAS=False and $\tilde{A}_I(t)>0.03$ g, then set IAS=True. If IAS=True and $\tilde{A}_I(t)<0.02$ g, then set IAS=False. Two thresholds used in this way implement hysteresis in a simple way to prevent rapid switching in the IAS.

Step 4. When IAS becomes True, a leg movement (LM) period begins. When IAS becomes false and remains false for more than 0.5 second, the LM period ends. Thus a contiguous time interval in which IAS=True, and surrounded by intervals in which IAS=False, comprises a leg movement (LM) period. However, if contiguous intervals for which IAS is True are separated by less than 0.5 second, the brief interval for which IAS was False is ignored.

Figure 8:
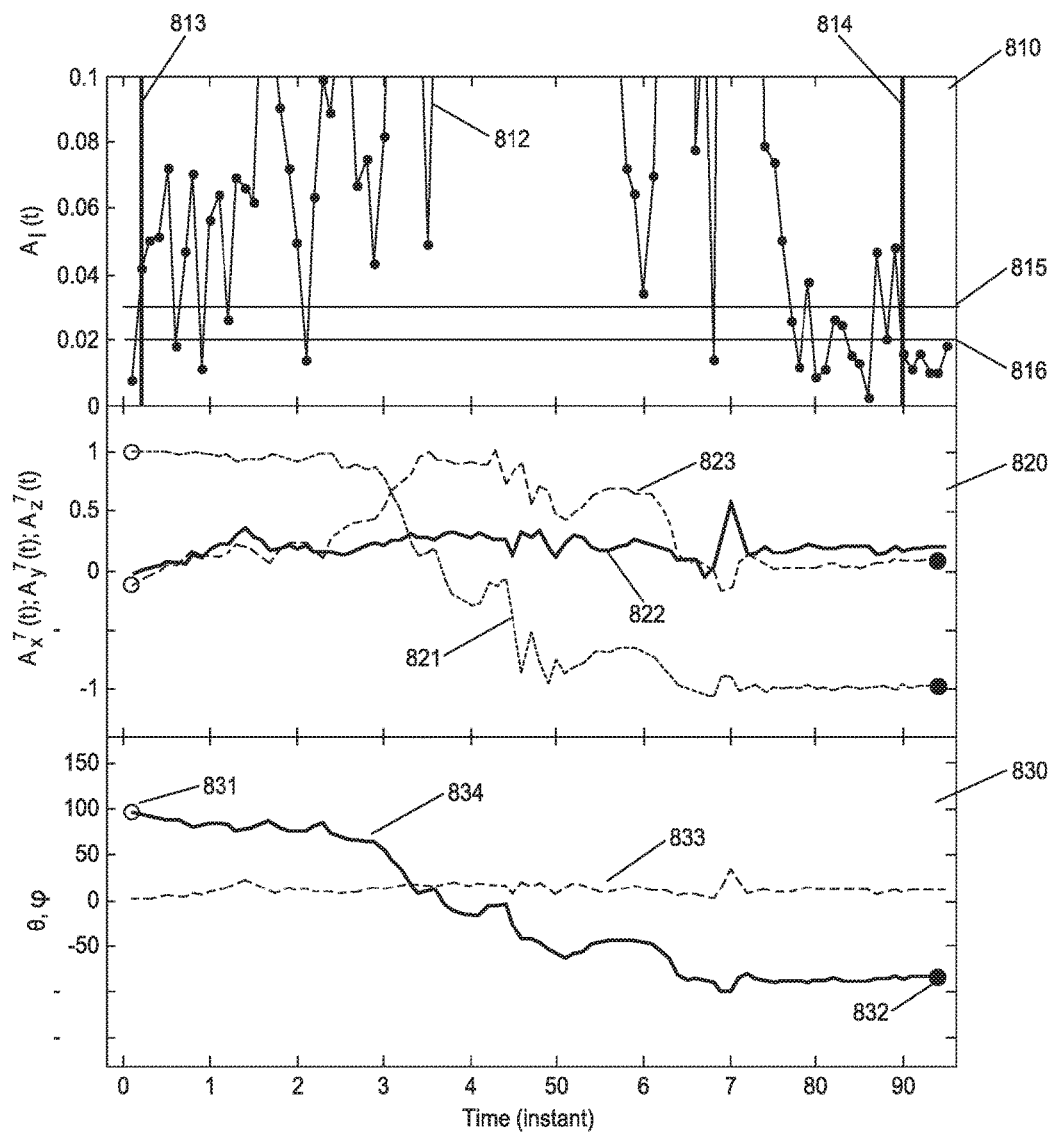
FIG. 8 is a schematic view showing the detection of a leg movement (LM) event, and calculation of the change Δφ in device rotational angle φ after (vs. before) the LM event.

The top panel (810) in FIG. 8 shows an example of the leg movement (LM) detection algorithm applied to real data. Time is measured in instants, i.e., steps of 0.1 second. The dots, and the line 812 connecting them, are the instantaneous accelerations $\tilde{A}_I(t)$. The vertical line 813 is when $\tilde{A}_I(t)$ first went above the threshold 815 (threshold value=0.03 g), at which point IAS was set to True. The instantaneous accelerations $\tilde{A}_I(t)$ fell below the second threshold 816 (threshold value=0.02 g) before the 90th instant. However, their durations were shorter than 0.5 second so they were ignored and the LM period continued. The vertical line 814 shows the instant when $\tilde{A}_I(t)$ first went below the second threshold 816 for more than 0.5 second so the LM period was terminated. The net result is an LM period with a duration of 89 instants (i.e., 8.9 seconds).

Body Roll Detector

In one preferred form of the invention, processor 515 of user state (i.e., leg orientation and leg motion) detector 500 is configured to function as a body roll detector.

More particularly, when the TENS device 100 (FIG. 9) is worn on the lower leg (i.e., upper calf 140) of a user, its accelerometer 152 will sense the projection of the gravity in its x-z plane when the user is in a recumbent position. The angle $\phi$ between the device x-axis and the gravity vector $-g$ can be calculated based on the projected gravity value in the x and z axis. Axis z' is aligned with the "big toe" direction of the user's leg to which the TENS device 100 is attached. Angle $\alpha$ between the device z-axis and the leg x'-axis is fixed when the TENS device is securely placed on the lower leg (i.e., upper calf 140) of the user. Finally, the body orientation angle $\beta$ defines the relative rotational position between the leg (defined as the direction in which the big toe is pointed, i.e., the z'-axis) and the earth gravity (z"-axis). The angular value remains the same when measuring from the x'-axis to the x"-axis. It is straightforward to derive the relationship between $\beta$ and $\phi$ as follows:

$$\beta=180-\alpha-\phi$$

Because the angle $\alpha$ is fixed, the leg rotation angle $\beta$ can be derived from the angle $\phi$ as measured by the accelerometer 152.

Some brief increases in activity that are classified as leg movement (LM) are associated with large changes in the roll angle $\phi$ measured by the TENS device 100. Rolls of sufficient magnitude are unlikely to involve only the leg, but rather are likely to indicate that the entire body is rolling over while in bed, e.g., from the left side to the right side, or from the back to the left side or the right side. Some leg movements (LMs) may therefore be classified as "body roll events".

In one preferred embodiment, a body roll detection algorithm is implemented by processor 515 in user state (i.e., leg orientation and leg motion) detector 500, using only the angle change $\Delta\phi$, in the following manner:

Step 1. For each LM period detected, select the raw acceleration vector A(t) in short windows before and after the leg movement. In a present invention, this window is an instant (0.1 seconds).

Step 2. Before and after each LM period, take the instant values of A(t) (not high-pass filtered) on each axis separately so as to obtain $A_x(t)$, $A_y(t)$, and $A_z(t)$.

Step 3. Using these values before and after the LM, compute the rotation angle $\phi(t)$=a tan 2$\{A_x(t), A_z(t)\}$. The inverse tangent function a tan 2 returns an angle in the range $-180°<\phi(t)\leq 180°$, i.e., a result in all four possible quadrants.

Step 4. Compute the change in rotational angle $\Delta\phi=\phi_{after}-\phi_{before}$. In order to facilitate comparison with a threshold (this is the "Threshold4" shown at step 924 in FIG. 10), this difference is put in the range $-180°<\Delta\phi\leq 180°$, i.e., if $\Delta\phi>180°$ then subtract 360°, but if $\Delta\phi\leq-180°$ then add 360°.

Step 5. Compare the absolute value $|\Delta\phi|$ with a threshold value. In the present invention, this threshold value is 50°, but other values may be used. If $|\Delta\phi|>50°$, then classify the LM event as a "body roll event".

The middle panel (820) in FIG. 8 shows this body roll detection algorithm applied to real data. The acceleration values $A_x(t)$, $A_y(t)$, and $A_z(t)$ are plotted in traces 821, 822, and 823. The y-axis component $A_y(t)\approx 0$ g throughout the event, consistent with the condition that lower leg elevation is in recumbent state. In contrast, $A_x(t)$ and $A_z(t)$ show significant activities, especially between time instants 30 and 70. In addition, the steady state value for $A_x(t)$ changed from +1 g (before the LM period) to -1 g (after the LM period), suggesting a body roll event.

The bottom panel (830) of FIG. 8 shows the calculation of the elevation angle $\theta$ (833) and the rotation angle $\phi$ (834) for each instant. The elevation angle $\theta\approx 0$ throughout the event, consistent with the lower leg being in recumbent elevation. In contrast, the rotation angle $\phi$ changes from $\phi\approx+90°$ (indicated by the empty circle 831) to $\phi\approx-88°$ (indicated by the filled circle 832). The angular change is $\Delta\phi\approx 178°$, consistent with a (rightward) roll of the entire body.

These body rolls may be reported directly to the user to inform them about their sleep patterns. In addition, because body roll events may be brief, the associated increase in activity may not be evident in the epoch average of activity, and therefore may not cause that epoch to be classified as awake. Although rolling over in bed may not indicate an awake state, it does indicate momentarily restless sleep. This novel approach for detecting body rolls by evaluating changes in roll angles associated with brief leg movement (LM) permits the differentiation of leg movement associated with no body rolls from leg movement associated with body rolls, and thus provides a finer description of sleep patterns that are helpful in clinical diagnosis.

In another preferred embodiment, rather than using single instants of A(t) before and after the LM to compute the angles $\phi$, the mean or median values of A(t) over several instants before and after the LM are used to improve robustness to noise.

In another preferred embodiment, a body roll detection algorithm is implemented by processor 515 of user state (i.e., leg orientation and leg motion) detector 500 using the angle change $\Delta\beta$ in the following manner. Consider a person lying on their back, with the TENS device placed on their right leg. Recalling that, with the TENS device placed on either leg, $\beta=0$ when the toes are pointed vertically upward, and $\beta$ increases with counterclockwise (CCW) rotation, therefore the most likely range of leg rotational positions is $-80°\leq\beta\leq 0°$. Any change in angle $\Delta\beta$ that remains within that range may not likely be associated with a body roll. In contrast, a change in angle $\Delta\beta$ from inside that range to outside that range is most likely associated with a body roll. In this way, using the change in angle $\Delta\beta$, the threshold for detecting a body roll may be adjusted depending upon the leg on which the device is placed. That is to say, in addition to the magnitude of the change $\Delta\beta$, the value of the leg rotation angle $\beta$ before and after the leg movement (LM), and the sign of the angle change $\Delta\beta$ across the leg movement (LM), may be used to improve performance of the body roll detector.

Static Body Rotational Position Detector

In one preferred form of the invention, processor 515 of user state (i.e., leg orientation and leg motion) detector 500 may be configured to function as a static body rotational position detector.

More particularly, users with sleep apnea are recommended not to sleep on their back.

Because of the limited rotational range of motion of the human hip, leg rotational position is highly correlated with body position, e.g., when sleeping on one's back, the toes of either foot are pointed upward above the horizontal plane to varying degrees, not likely exactly on the horizontal plane, and never below the horizontal plane. This observation, together with the placement of the novel TENS device on the upper calf of the user, allows an innovative addition to sleep analysis.

The time scale of an "epoch" equal to one minute, and the epoch-averaged non-high-pass filtered acceleration values $\overline{A}_{X,T}(t)$, $\overline{A}_{Y,T}(t)$, and $\overline{A}_{Z,T}(t)$ were introduced above in the section entitled "Leg Elevation Detection". Because it is sufficient to report the time spent sleeping on the back at the resolution of one minute, these epoch-averaged acceleration values may be advantageously used in the following manner to detect static body rotational position.

Consistent with the roll detector definition of the rotational position angle $\phi$, let $\phi_{T=a\ tan}\ 2\{\overline{A}_{X,T}(t), \overline{A}_{Z,T}(t)\}$ as before, where $\overline{A}_{X,T}(t)$ and $\overline{A}_{Z,T}(t)$ are raw (i.e., not high-pass filtered) accelerations averaged over an epoch T. Let $\beta_T$=the angle of the toes relative to the vertical. The relation between $\phi_T$ and $\beta_T$ depends upon the rotational placement of the TENS device on the upper calf of the user, denoted $\alpha$. Because the electrode gel 444 is sticky and the strap 110 is supportive, the TENS device does not move on the user's leg once it is placed onto the upper calf 140, therefore the angle $\alpha$ is constant as long as the TENS device is on the leg of the user.

Figure 9:
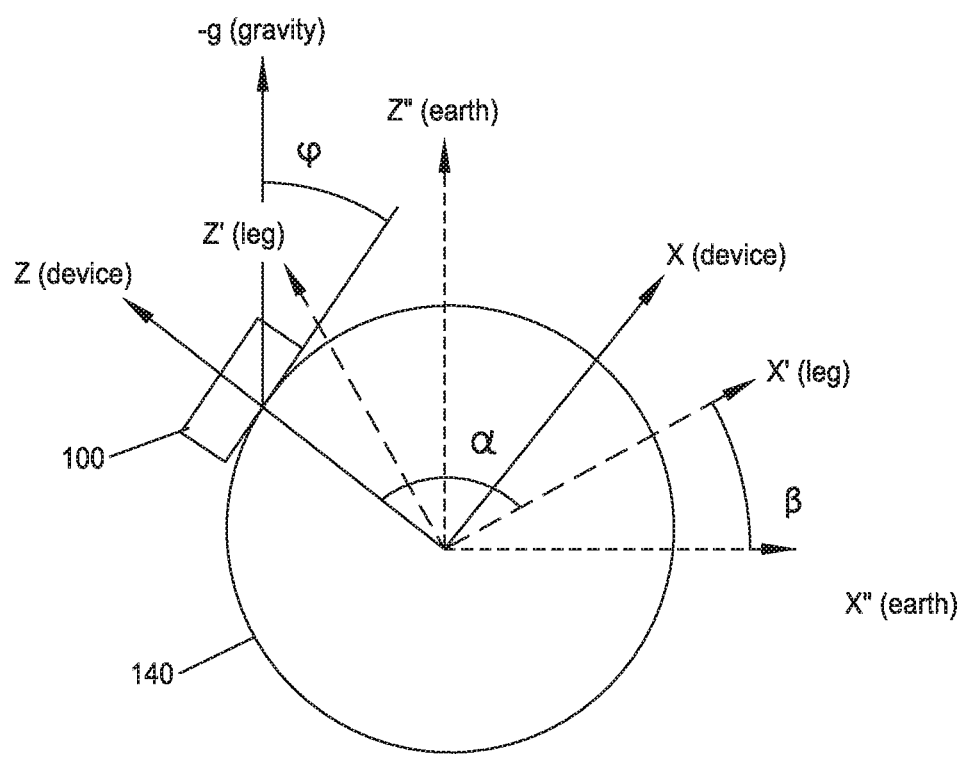
FIG. 9 is a schematic view showing the mathematics for relating the accelerometer rotational angle φ (measured by the accelerometer) to the leg rotational angle β, via a third angle a representing the rotational position of the novel TENS device on the upper calf of a user.

Looking now at FIG. 9, the double-primed coordinate system (i.e., x", y", z", with y" not being seen in FIG. 9 since it extends down the axis of the leg) is fixed to the Earth with gravity along the vertical, the single-primed coordinate system (i.e., x', y', z', with y' not being seen in FIG. 9 since it extends down the axis of the leg) is fixed to the leg, and the unprimed coordinate system (i.e., x, y, z, with y not being seen in FIG. 9 since it extends down the axis of the leg) is fixed to the TENS device measuring $\overline{A}_{X,T}(t)$ and $\overline{A}_{Z,T}(t)$. The Earth coordinate system has its z"-axis along the vertical, the leg coordinate system has its z'-axis in the direction of the toes, and the leg rotational angle $\beta$ is the angle between the Earth x"-axis and leg x'-axis. The TENS device angle $\alpha$ is the location of the TENS device on the leg measured from the leg x'-axis. Using knowledge of the accelerometer axes in the TENS device, and standard techniques of geometry including the identification of similar triangles, it will be evident to those skill in the art that these angles are related simply by $\beta=180-\alpha-\phi$. In each epoch, therefore, these angles are related simply by $\beta_T=180-\alpha\phi_T$.

In a preferred embodiment, the following simple procedure is used by processor 515 of user state (i.e., leg orientation and leg motion) detector 500 to determine whether the user is on-back through an estimation of the angle $\beta$.

Step 1. The user places the TENS device on the lower leg of the user and fastens the strap 110 snugly around their upper calf 140, lies recumbent with the leg nearly horizontal, points their toes vertically upward, and remains still.

Step 2. The user indicates to the TENS device that the aforementioned conditions have been met. This indication may take the form of a series of button presses (e.g., with button 106), a series of taps on compartment 102 detected by the accelerometer 152, or an indication on a smartphone 860 in communication with the TENS device 100.

Step 3: With the toes pointed upright, $\beta\approx0$, therefore it is trivial to estimate $\hat{\alpha}=180-\hat{\phi}$ where $\hat{\phi}$ is estimated from accelerometer data acquired during the toe-up period. In order to facilitate calculations, put this difference in the range $-180°<\hat{\alpha}\leq180°$, i.e., if $\hat{\alpha}>180°$ then subtract 360°, but if $\hat{\alpha}\leq-180°$ then add 360°.

Step 4: In every epoch ending at time T, use this value of $\hat{\alpha}$ to compute $\beta_T=180-\hat{\alpha}-\phi_T$. In order to facilitate comparisons with a threshold, put this difference in the range $-180°<\beta_T\leq180°$, i.e., if $\beta_T>180°$ then subtract 360°, but if $\beta_T\leq-180°$ then add 360°.

Step 5: Define a range of values for $\beta_T$ that correspond to the user lying or sleeping on their back. In a preferred embodiment, classify every epoch for which $-80°<\beta_T<80°$ as "on-back". This range is symmetrical so the algorithm works for placement on either leg. Avoiding ±90° by 10° excludes the values likely to be encountered when a user lies or sleeps on their side. In another preferred embodiment, the thresholds (which would reside at step 930 in FIG. 10) depend upon the leg on which the device is placed. For example, if the device is placed on the left leg, the most likely range of angles while lying on the back is $0°<\beta_T<80°$. Alternatively, if the device is placed on the right leg, the most likely range of angles while lying on the back is $-80°<\beta_T<0°$.

Step 6: If the user with sleep apnea selects this option for TENS device 100, then when the user is determined to be asleep, i.e., recumbent with low activity, the TENS device notifies the user if they are on their back for more than some set amount of time, e.g., a few minutes. This indication can be in the form of a vibration of the TENS device itself, or an alarm on their smartphone 860, for example.

Step 7: After determining the span(s) of minutes in which the user was likely to be asleep, i.e., recumbent with low activity, determine the fraction of minutes in which the user was determined to be on their back. Report this percentage to this user, e.g., with smartphone 860.

Exemplary Operation

Figure 10:
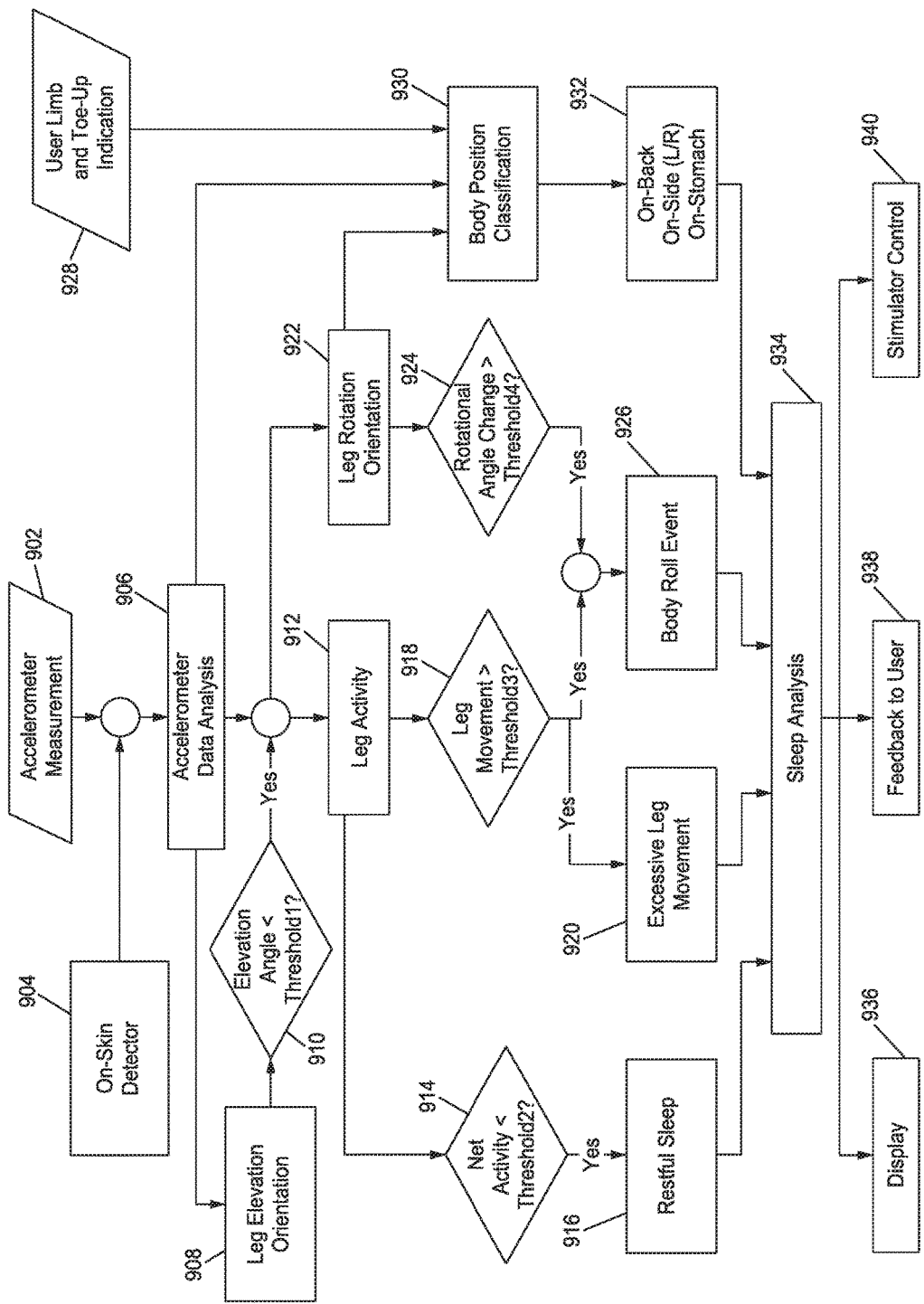
FIG. 10 is a schematic flow chart showing exemplary operation of the novel TENS device, including its user state (i.e., leg orientation and leg motion) detector.

In one preferred form of the invention, TENS device 100, including its user state (i.e., leg orientation and leg motion) detector 500, its processor 515 and its controller 520, are programmed to operate in the manner shown in the flowchart of FIG. 10.

More particularly, when TENS device 100 is secured to the upper calf 140 of the user and turned on, user state (i.e., leg orientation and leg motion) detector 500 collects data from accelerometer 152, real-time clock 505 and ambient light detector 510, as shown at step 902. In addition, on-skin detector 521 confirms that electrode array 120 of TENS device 100 is in contact with the user's skin, as shown at step 904 (and hence confirms that TENS device 100 is secured to the upper calf 140 of the user).

Processor 515 analyzes data from accelerometer 152, real-time clock 505 and ambient light detector 510, as shown at step 906.

Processor 515 determines the user's leg elevation orientation, as shown at step 908, and determines if the user is in bed by comparing elevation angle with a threshold (i.e., "Threshold4"), as shown at step 910.

If processor 515 determines that the user is in bed, processor 515 determines the user's leg activity, as shown at step 912.

The user's leg activity is compared against a threshold (i.e., "Threshold1"), as shown at step 914, and, if the user's leg activity is below that threshold, processor 515 determines that the user is in a restful sleep, as shown at step 916.

Processor 515 also compares the user's leg activity (determined at step 912) against another threshold (i.e., "Threshold2"), as shown at step 918, and, if the user's leg activity is above that threshold, processor 515 determines that the user has excessive leg movement, as shown at step 920.

In addition to the foregoing, processor 515 also determines the user's leg rotation orientation, as shown at step 922, and compares the change in the angle of the user's leg rotation against another threshold (i.e., "Threshold3"), as shown at step 924, and, if the change in the angle of the user's leg rotation is above that threshold, and if the user's leg movement exceeds a threshold (i.e., "Threshold2") as shown at step 918, processor 515 determines that a body roll event has occurred, as shown at step 926.

Also, processor 515 looks at the user's leg rotation orientation, as determined at step 922, the accelerometer data analysis, as determined at step 906 and the user's user limb and toe-up indication, as determined at step 928, and determines the user's body position classification, as shown at step 930. Processor 515 then characterizes the user's position as "on back", "on side (left/right)" or "on stomach", as shown at step 932.

The information derived at steps 916, 920, 926 and 932 is then utilized by processor 515 to analyze the user's sleep session, as shown at step 934. The results of this sleep analysis (as determined at step 934) may then be displayed (as shown at step 936), used to provide feedback to the user or the user's caregiver (as shown at step 938) and/or used to direct controller 520 (as shown at step 940) to modulate the stimulation current provided by TENS device 100.

Modifications of The Preferred Embodiments

It will be appreciated that the present invention provides a transcutaneous electrical nerve stimulator with automatic monitoring of leg activities and leg orientations. Leg orientations include leg elevation and leg rotation state, and changes in leg elevation and leg rotation states. The TENS stimulator may be pre-programmed to modify its operations in response to the detected user leg activities and leg positions during bed time. In addition, leg orientation and leg activities are used to assess sleep quality and sleep position, all are important aspects to improve sleep and health. Leg activity patterns can also be used to diagnose sleep disorders such as periodic leg movement and the TENS stimulator can be used to alleviate excessive leg movement activities that are disruptive to sleep.

The present invention can also be realized without the nerve stimulation functionality. Body movement and position can be monitored and quantified using the present invention without the need of nerve stimulation. The monitoring apparatus (device) can also be placed in other body positions like upper arm of either limb.

Furthermore, it should be understood that many additional changes in the details, materials, steps and arrangements of parts, which have been herein described and illustrated in order to explain the nature of the present invention, may be made by those skilled in the art while still remaining within the principles and scopes of the invention.

What is claimed is:

1. Apparatus for providing transcutaneous electrical nerve stimulation (TENS) therapy to a user, said apparatus comprising:
   a housing;
   an application unit for providing mechanical coupling between said housing and the user's body;
   a stimulation unit for electrically stimulating at least one nerve of the user;
   a sensing unit for (i) sensing the user's body movement and body orientation to determine whether the user is in a sleep state or a wake state, and (ii) analyzing the sleep state of the user; and
   a feedback unit for at least one of (i) providing the user with feedback in response to the analysis of the sleep state of the user, and (ii) modifying the electrical stimulation provided to the user in response to the analysis of the sleep state of the user.

2. Apparatus according to claim 1 wherein said application unit is a flexible band.

3. Apparatus according to claim 1 wherein said application unit communicates whether said housing is mechanically coupled to the user's body.

4. Apparatus according to claim 3 wherein a mechanical element determines whether said housing is mechanically coupled to the user's body.

5. Apparatus according to claim 4 wherein said mechanical element is a tension gauge.

6. Apparatus according to claim 3 wherein an electrical element determines whether said housing is mechanically coupled to the user's body.

7. Apparatus according to claim 6 wherein said electrical element measures the voltage value of a voltage divider circuit formed by said housing and the user's body.

8. Apparatus according to claim 1 wherein said sensing unit uses data from an electromechanical sensor.

9. Apparatus according to claim 8 wherein whether said housing is mechanically coupled to the user's body determines the usability of the data from said electromechanical sensor.

10. Apparatus according to claim 8 wherein said electromechanical sensor is an accelerometer.

11. Apparatus according to claim 1 wherein said sensing unit determines the user's body orientation state with an analysis unit operating on earth gravitational acceleration measurements.

12. Apparatus according to claim 11 wherein the user's body orientation comprises one from the group consisting of upright and recumbent.

13. Apparatus according to claim 12 wherein said analysis unit is a programmable microprocessor that averages projections of the gravitational acceleration measurements on an axis of said electromechanical sensor and compares the average with a threshold.

14. Apparatus according to claim 13 wherein said axis is aligned with the longitudinal direction of the user's body.

15. Apparatus according to claim 13 wherein said threshold is one half of the standard earth gravitational acceleration value.

16. Apparatus according to claim 13 wherein said average is calculated over a period of one-minute.

17. Apparatus according to claim 13 wherein the user's body orientation is determined to be recumbent when said average is below said threshold.

18. Apparatus according to claim 8 wherein said sensing unit determines the user's movement with an analysis unit operating on said data from said electromechanical sensor.

19. Apparatus according to claim 18 wherein said movement is considered to be active when a processed feature of said data is determined to be inside a target range.

20. Apparatus according to claim 19 wherein said processed feature is an average of a combination of filtered components of the data from said electromechanical sensor.

21. Apparatus according to claim 20 wherein said combination is the square root of the sum of the squares of said filtered components.

22. Apparatus according to claim 20 wherein the filtering is to remove the static earth gravity component from the data from said electromechanical sensor.

23. Apparatus according to claim 20 wherein said component is each individual axis data from said electromechanical sensor.

24. Apparatus according to claim 19 wherein said target range includes all values above a threshold.

25. Apparatus according to claim 19 wherein said target range has a boundary incorporating a hysteresis band.

26. Apparatus according to claim 25 wherein the width of said hysteresis band depends upon the estimated noise level of the data from said electromechanical sensor.

27. Apparatus according to claim 1 wherein the body orientation is a rotational orientation in a plane perpendicular to the longitudinal axis of the user's body.

28. Apparatus according to claim 27 wherein said sensing unit uses data from an electromechanical sensor, and further wherein the rotational orientation is estimated by an analysis of the output of said electromechanical sensor.

29. Apparatus according to claim 28 wherein the output of said electromechanical sensor is an average of the projections of earth gravity onto a plane perpendicular to the longitudinal axis of the user's body.

30. Apparatus according to claim 29 wherein said analysis comprises estimating an angle formed by said average of the projections of earth gravity.

31. Apparatus according to claim 30 wherein a calibrated body rotational orientation is based on the estimated angle and a rotational orientation angle at a known body orientation.

32. Apparatus according to claim 31 wherein said known body orientation is with the user lying on their back with their big toe pointing upwards.

33. Apparatus according to claim 1 wherein said sensing unit uses data from an electromechanical sensor, wherein whether said housing is mechanically coupled to the user's body determines the usability of the data from said electromechanical sensor, wherein said electromechanical sensor is an accelerometer, and wherein said sensing unit determines the user's body orientation with an analysis unit operating on earth gravitational acceleration measurements, and wherein the user's body orientation comprises one from the group consisting of upright and recumbent;

and further wherein said sensing unit determines the user's movement with an analysis unit operating on said data from said electromechanical sensor, and further wherein said movement is considered to be active when a processed feature of said data is determined to be inside a target range; and wherein said feedback unit calculates the accumulative time when the user's body orientation is recumbent.

34. Apparatus according to claim 33 wherein said feedback unit calculates the accumulative time when the user's movement is not active and the user's body orientation is recumbent.

35. Apparatus according to claim 33 wherein said feedback unit calculates a distribution of pair-wise difference of the user's body rotational orientation angles.

36. Apparatus according to claim 35 wherein each pair of angles are measured when the user's body orientation is recumbent and immediately before and after the user's movement is active.

37. Apparatus according to claim 35 wherein said feedback unit calculates a time duration when the user's calibrated body rotational orientation angle is determined to be within a target range.

38. Apparatus according to claim 37 wherein said target range is independent of the limb designation.

39. Apparatus according to claim 37 wherein said target range is dependent on the limb designation.

40. Apparatus according to claim 37 wherein an output of said feedback unit is activated when the user's calibrated body rotational orientation is inside said target range.

41. Apparatus according to claim 35 wherein an output of said feedback unit is activated when said distribution meets a set of criteria.

42. Apparatus according to claim 41 wherein said set of criteria is that a fraction of the pair-wise differences with values exceeding a first threshold is greater than a second threshold.

43. Apparatus according to claim 37 wherein an output of said feedback unit is activated when said time duration exceeds a threshold.

44. Apparatus according to claim 1 wherein said feedback is the provision of mechanical vibrations to the user.

45. Apparatus according to claim 1 wherein said feedback is the provision of electrical stimulation to the user.

46. Apparatus according to claim 1 wherein said feedback comprises modulation of said stimulation unit.

47. Apparatus according to claim 46 wherein said modulation results in a modification of the TENS stimulation intensity.

48. Apparatus according to claim 46 wherein said modulation results in a modification of the TENS stimulation frequency.

49. Apparatus according to claim 46 wherein said modulation results in a modification of the TENS stimulation onset time.

50. Apparatus according to claim 1 wherein said feedback is an alert delivered to the user through at least one selected from the group consisting of a smartphone and another connected device.

51. A method for applying transcutaneous electrical nerve stimulation to a user, said method comprising the steps of:
    applying a stimulation unit and a sensing unit to the user's body;
    using the stimulation unit to deliver electrical stimulation to the user to stimulate one or more nerves;
    analyzing electromechanical sensing data from the sensing unit to quantify the user's body orientation and body activity levels to determine whether the user is in a sleep state or a wake state and to determine the quality and duration of the sleep state; and
    modifying the electrical stimulation delivered by the stimulation unit based on the user's body orientation and body activity levels.

52. Apparatus for monitoring the sleep patterns of a user, said apparatus comprising:
    a housing;
    an application unit for providing mechanical coupling between said housing and the user's body;
    a sensing unit disposed within the housing for (i) sensing the user's body movement and body orientation to determine whether the user is in a sleep state or a wake state, and (ii) analyzing the sleep state of the user; and
    a feedback unit for providing the user with feedback in response to the analysis of the sleep state of the user.

53. A method for monitoring the sleep patterns of a user, said method comprising of the steps of:
    applying a sensing unit and a feedback unit to the user body;
    using the sensing unit to determine the user's body movement and body orientation to (i) determine whether the user is in a sleep state or a wake state, and (ii) analyze the sleep state of the user; and providing the user with feedback via said feedback unit in response to the analysis of the sleep state of the user.

54. Apparatus for providing transcutaneous electrical nerve stimulation (TENS) therapy to a user, said apparatus comprising:
a housing;
an application unit for providing mechanical coupling between said housing and the user's leg;
a stimulation unit for electrically stimulating at least one nerve of the user; and
a sensing unit for (i) sensing the user's leg orientation and leg motion to determine whether the user is in a sleep state or a wake state, wherein sensing the user's leg orientation comprises determining the user's leg elevation and leg rotation, and further wherein sensing the user's leg motion comprises determining the user's net activity and leg movements, and (ii) analyzing the sleep state of the user; and
a controller for modulating said stimulation unit based on the determinations made by said sensing unit.

55. Apparatus for providing transcutaneous electrical nerve stimulation (TENS) therapy to a user, said apparatus comprising:
a housing;
an application unit for providing mechanical coupling between said housing and the user's body;
a stimulation unit for electrically stimulating at least one nerve of the user;
a sensing unit for sensing the user's body movement and body orientation; and
a feedback unit for providing the user with feedback based on the user's sensed body movement and body orientation;
wherein said sensing unit determines the user's body orientation state with an analysis unit operating on earth gravitational acceleration measurements;
wherein the user's body orientation comprises one from the group consisting of upright and recumbent;
wherein said analysis unit is a programmable microprocessor that averages projections of the gravitational acceleration measurements on an axis of said electromechanical sensor and compares the average with a threshold; and
further wherein said threshold is one half of the standard earth gravitational acceleration value.

56. Apparatus for providing transcutaneous electrical nerve stimulation (TENS) therapy to a user, said apparatus comprising:
a housing;
an application unit for providing mechanical coupling between said housing and the user's body;
a stimulation unit for electrically stimulating at least one nerve of the user;
a sensing unit for sensing the user's body movement and body orientation; and
a feedback unit for providing the user with feedback based on the user's sensed body movement and body orientation;
wherein said sensing unit uses data from an electromechanical sensor;
wherein said sensing unit determines the user's movement with an analysis unit operating on said data from said electromechanical sensor;
wherein said movement is considered to be active when a processed feature of said data is determined to be inside a target range; and
further wherein said target range has a boundary incorporating a hysteresis band.

57. Apparatus according to claim 56 wherein the width of said hysteresis band depends upon the estimated noise level of the data from said electromechanical sensor.

* * * * *